United States Patent
Grant, III et al.

(10) Patent No.: US 6,713,455 B2
(45) Date of Patent: Mar. 30, 2004

(54) 6-O-CARBAMATE-11,12-LACTO-KETOLIDE ANTIMICROBIALS

(75) Inventors: Eugene B. Grant, III, Flemington, NJ (US); Todd C. Henninger, High Bridge, NJ (US); Mark J. Macielag, Branchburg, NJ (US); Deodialsingh Guiadeen, Linden, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/244,184

(22) Filed: Sep. 16, 2002

(65) Prior Publication Data

US 2003/0125267 A1 Jul. 3, 2003

Related U.S. Application Data

(60) Provisional application No. 60/322,762, filed on Sep. 17, 2001.

(51) Int. Cl.[7] .......................... A61K 31/70; C07H 17/08
(52) U.S. Cl. .............................. 514/29; 536/7.2; 536/7.4
(58) Field of Search ...................... 536/7.4, 7.2; 514/29

(56) References Cited

U.S. PATENT DOCUMENTS

| | | | |
|---|---|---|---|
| 4,826,820 | A | 5/1989 | Brain |
| 5,444,051 | A | 8/1995 | Agouridas et al. |
| 5,559,256 | A | 9/1996 | Gordon et al. |
| 5,561,118 | A | 10/1996 | Agouridas et al. |
| 5,770,579 | A | 6/1998 | Agouridas et al. |
| 5,866,549 | A | 2/1999 | Or et al. |

FOREIGN PATENT DOCUMENTS

| | | |
|---|---|---|
| EP | 0 216 169 A2 | 4/1987 |
| EP | 1 114 826 A2 | 7/2001 |
| WO | WO 95/26360 A1 | 10/1995 |
| WO | WO 97/17356 A1 | 5/1997 |
| WO | WO 97/36896 A1 | 10/1997 |
| WO | WO 98/09978 A1 | 3/1998 |
| WO | WO 98/21188 A1 | 5/1998 |
| WO | WO 98/28264 A1 | 7/1998 |
| WO | WO 99/02524 A1 | 1/1999 |
| WO | WO 99/21864 A1 | 5/1999 |
| WO | WO 99/21871 A1 | 5/1999 |
| WO | WO 99/35157 A1 | 7/1999 |
| WO | WO 00/62783 A2 | 10/2000 |
| WO | WO 00/63224 A2 | 10/2000 |
| WO | WO 00/63225 A2 | 10/2000 |
| WO | WO 00/75156 A1 | 12/2000 |
| WO | WO 02/16380 A1 | 2/2002 |
| WO | WO 02/50092 A1 | 6/2002 |

OTHER PUBLICATIONS

Daubresse, N. et al.: "Phase Transfer Wittig Reaction with 1,3–Dioxolan–2–yl–methyltriphenyl phosphonium Salts: an Efficient Method for Vinylogation of Aromatic Aldehydes", Tetrahedron 54 (1998), pp. 10761–10770.

Franchett, P. et al.: "Structure–Activity Relationships in Reactivators of Organophosphorus–Inhibited Acetylcholinesterase. 9. N–Heterocyclic Acraldoximes Methiodides", J. of Med. Chem, 1975, vol. 18, No. 8, pp 839–842.

Hashizume, H. et al.: "Synthesis and Biological Activities of New HMG–COA Synthase Inhibitors: 2–Oxetanones with a Side Chain Containing Biphenyl, Terphenyl or Phenylpyridine", Heterocycles, vol. 38, No. 7, 1994, pp 1551–1571.

Hauske, J.R. et al.: "Synthesis of 10,11–Anhydroerythromycin", J. Org. Chem. 1982, 47, pp. 1595–1596.

Kim, M.S. et al.: "Photophysical Properties and Conformational Equilibrium of trans–6–Styrylquinoxaline", Photochem. and Photobiol. vol. 54, No. 1, pp. 7–15.

Kingsbury, W.D. et al.: "Synthesis of Structural Analogs of Leukotriene $B_4$ and Their Receptor Binding Activity", J. Med. Chem. 1993, 36, pp. 3308–3320.

Parrain, J.L. et al.: "1–Tributylstannyl–3,3–diethoxyprop–1–ene as a $d^3$ Acrolein Equivalent", J. Chem. Soc. Perkin Trans. 1, 1990, pp 187–189.

Tanaka, A. et al.: "Inhibitors of Acyl–CoA:Cholesterol O–Acyltransferase. 2. Identification and Structure–Activity Relationships of a Novel Series of N–Alkyl–N–(heteroaryl–substituted benzyl)–N'–arylureas[1]", J. Med. Chem. 1998, 41, pp. 2390–2410.

Zwaagstra, M.E., et al.: "Synthesis and Structure–Activity Relationships of Carboxylated Chalcones: A Novel Series of $CysLT_1$ ($LTD_4$) Receptor Antagonists", J. Med. Chem. 1997, 40, pp. 1075–1089.

Angew. Chem. 1975, 87, pp. 486–487. [Note: Article is in German language. Look to the structures for relativity].

*Primary Examiner*—Elli Peselev
(74) *Attorney, Agent, or Firm*—Joseph S. Kentoffio

(57) ABSTRACT

6-O-Carbamate-11,12-lacto-ketolide antimicrobials of the formula:

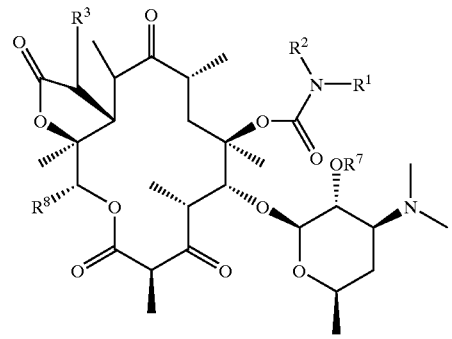

wherein $R^1$, $R^2$, $R^3$ $R^7$, and $R^8$ are as described herein and in which the substituents have the meaning indicated in the description. These compounds are useful as antibacterial agents.

24 Claims, No Drawings

6-O-CARBAMATE-11,12-LACTO-KETOLIDE ANTIMICROBIALS

This application claims the benefit under 35 U.S.C. §119(e) of provisional application Ser. No. 60/322,762, filed on Sep. 17, 2001, which is incorporated herein by reference.

FIELD OF THE INVENTION

The present invention relates to the field of macrolide compounds having antibacterial activity, pharmaceutical compositions containing the compounds, and methods of treating bacterial infections with the compounds.

BACKGROUND OF THE INVENTION

Erythromycins are well-known antibacterial agents widely used to treat and prevent bacterial infection caused by Gram-positive and Gram-negative bacteria. However, due to their low stability in acidic environment, they often carry side effects such as poor and erratic oral absorption. As with other antibacterial agents, bacterial strains having resistance or insufficient susceptibility to erythromycin have developed over time and are identified in patients suffering from such ailments as community-acquired pneumonia, upper and lower respiratory tract infections, skin and soft tissue infections, meningitis, hospital-acquired lung infections, and bone and joint infections. Particularly problematic pathogens include methicillin-resistant *Staphylococcus aureus* (MRSA), vancomycin-resistant enterococci (VRE) and penicillin- and macrolide-resistant *Streptococcus pneumoniae*. Therefore, continuing efforts are called for to identify new erythromycin derivative compounds with improved antibacterial activity, and/or unanticipated selectivity against various target microorganisms, particularly erythromycin-resistant strains.

The following references relate to various erythromycin derivatives disclosed as having antibacterial activity:

EP 216,169 and U.S. Pat. No. 4,826,820 to Brain et al. disclose antibacterially active 6-carbamate erythromycin derivatives stated to "have antibacterial properties, in particular against Gram-positive bacteria but also against some Gram-negative bacteria."

U.S. Pat. No. 5,444,051, U.S. Pat. No. 5,561,118, and U.S. Pat. No. 5,770,579, all to Agouridas et al., disclose erythromycin compounds such as those of the formula

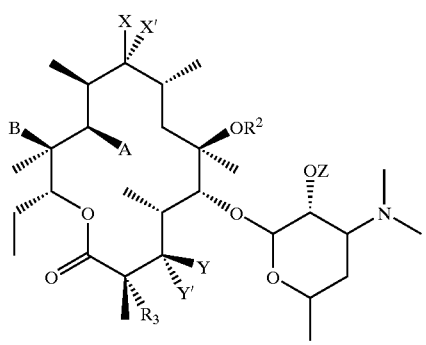

wherein substituents are as described in the respective references, which are all stated to be useful as antibiotics.

U.S. Pat. No. 5,866,549 to Or et al. and WO 98/09978 (Or et al.) disclose 6-O-substituted ketolides stated to have increased acid stability relative to erythromycin A and 6-O-methyl erythromycin A and enhanced activity toward gram negative bacteria and macrolide resistant gram positive bacteria.

WO 97/17356 (Or et al.) discloses tricyclic erythromycin derivatives stated to be useful in the treatment and prevention of bacterial infections.

WO 99/21871 (Phan et al.) discloses 2-halo-6-O-substituted ketolide derivatives of the formula

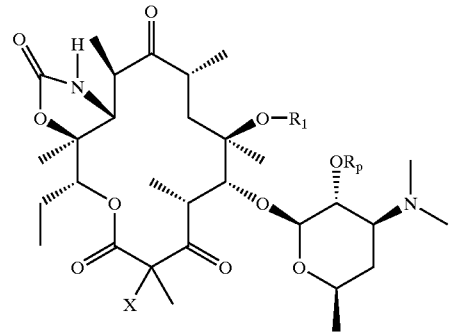

wherein substituents are as described in the respective reference, which are stated to possess antibacterial activity.

WO 99/21864 (Or et al.) discloses 6,11-bridged erythromycin derivatives stated to have antibacterial activity.

WO 00/75156 (Phan et al.) discloses a 6-O-carbamate ketolide compound stated to be useful for treatment and prevention of infections in a mammal.

SUMMARY OF THE INVENTION

The invention provides compounds of Formula 1:

Formula 1

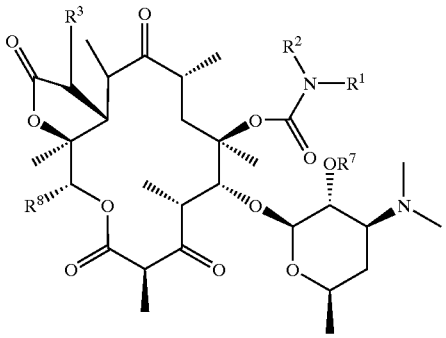

wherein:

$R^1$ and $R^2$ are independently selected from hydrogen, optionally substituted $C_1$–$C_8$-alkyl, optionally substituted —$CH_2$—$C_{2-8}$alkenyl, and optionally substituted —$CH_2$—$C_{2-8}$alkynyl, wherein the substituents are selected from the group consisting of alkyl, alkenyl, alkynyl, cycloalkyl, aryl, heteroaryl, substituted aryl, substituted heteroaryl, hydroxy, and $C_{1-8}$alkoxy;

$R^3$ is selected from hydrogen, $OR^4$, $SR^4$, and $NR^5R^6$, wherein $R^4$, $R^5$, and $R^6$ are independently selected from the group consisting of $C_{1-8}$alkyl, $C_{3-8}$alkenyl, and $C_{3-8}$alkynyl, said $C_{1-8}$alkyl, $C_{3-8}$alkenyl, and $C_{3-8}$alkynyl being optionally substituted with one or more substituents selected from the group consisting of aryl, substituted aryl, heteroaryl, substituted heteroaryl, hydroxy, and $C_{1-6}$alkoxy;

$R^7$ is hydrogen or a hydroxy protecting group; and $R^8$ is selected from hydrogen, alkyl, $C_2$–$C_{10}$-alkenyl, $C_2$–$C_{10}$-alkynyl, aryl, heteroaryl, heterocyclo, aryl ($C_1$–$C_{10}$)alkyl, aryl($C_2$–$C_{10}$)alkenyl, aryl($C_2$–$C_{10}$) alkynyl, heterocyclo($C_1$–$C_{10}$)alkyl, heterocyclo ($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

or an optical isomer, enantiomer, diastereomer, racemate or racemic mixture thereof, or a pharmaceutically acceptable salt, esters or pro-drugs thereof.

Compounds of Formula 1 are useful as antibacterial agents for the treatment of bacterial infections in a subject such as human and animal.

The present invention is also directed to a method of treating a subject having a condition caused by or contributed to by bacterial infection, which comprises administering to said subject a therapeutically effective amount of the compound of Formula 1.

The present invention is further directed to a method of preventing a subject from suffering from a condition caused by or contributed to by bacterial infection, which comprises administering to the subject a prophylactically effective amount of the compound of Formula 1.

Other objects and advantages will become apparent to those skilled in the art from a review of the ensuing specification.

DETAILED DESCRIPTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon—carbon double bond. "Alkynyl" refers to a straight or branched chain hydrocarbon with at least one carbon—carbon triple bound. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. The alkyl, alkenyl, alkynyl, cycloalkyl group and alkoxy group may be independently substituted with one or more members of the group including, but not limited to, halogen, alkyl, alkenyl, alkynyl, cycloalkyl, alkoxy, oxo, aryl, heteroaryl, heterocyclo, CN, nitro, —$OCOR_a$, —$OR_a$, —$SR_a$, —$SOR_a$, —$SO_2R_a$, —$COOR_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from H, alkyl, alkenyl, alkynyl, cycloalkyl, aryl, heteroaryl, heterocyclo, aralkyl, heteroaralkyl, and heterocycloalkyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo or iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with aryl, heteroaryl, halogen, OH, CN, mercapto, nitro, amino, $C_1$–$C_8$-alkyl, $C_2$–$C_8$-alkenyl, $C_1$–$C_8$-alkoxyl, $C_1$–$C_8$-alkylthio, $C_1$–$C_8$-alkyl-amino, di($C_1$–$C_8$-alkyl) amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl. "Bz" denotes benzoyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrrolyl, pyrazolyl, imidazolyi, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, indazolyl, indolizinyl, benzofuryl, cinnolinyl, quinoxalinyl, pyrrolopyridinyl, furopyridinyl (such as furo[2,3-c] pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with aryl, heteroaryl, halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl) amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully saturated, partially saturated, or non-aromatic cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl;

2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzoth iopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like.

Substituted aryl, substituted heteroaryl, and substituted heterocycle may also be substituted with a second substituted aryl, a second substituted heteroaryl, or a second substituted heterocycle to give, for example, a 4-pyrazol-1-yl-phenyl or 4-pyridin-2-yl-phenyl.

Designated numbers of carbon atoms (e.g., $C_1$–$C_8$ or $C_{18}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; pivaloyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl; acyl and aroyl such as acetyl, benzoyl, pivaloylbenzoyl, 4-methoxybenzoyl, 4-nitrobenzoyl and aliphatic acylaryl.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, $Ca(OH)_2$, $Al(OH)_3$, piperidine, morpholine, ethylamine, triethylamine and the like.

Included within the scope of the invention are the hydrated forms of the compounds which contain various amounts of water, for instance, the hydrate, hemihydrate, and sesquihydrate forms. The present invention also includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" includes, without limitation, any animal or artificially modified animal. As a particular embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals.

Preferably, compounds of Formula 1 wherein $R^1$ and $R^2$ are independently selected from hydrogen, substituted $C_{1-8}$alkyl, optionally substituted —$CH_2$—$C_{2-8}$alkenyl, and substituted —$CH_2$—$C_{2-8}$alkynyl, wherein the substituents are selected from aryl, substituted aryl, heteroaryl, substituted heteroaryl, are embodiments of the present invention for such purposes. Particularly, $R^3$ is hydrogen or $OR^4$. Particularly, $R^7$ is hydrogen. Particularly, $R^8$ is ethyl.

Compounds of Formula 1 wherein $R^1$ and $R^2$ are independently selected from hydrogen and substituted —$CH_2$—$C_{2-8}$-alkenyl, wherein the substituents are substituted aryl or substituted heteroaryl, are preferred embodiments of the present invention. Particularly, $R^3$ is hydrogen, and $R^1$ and $R^2$ are independently selected from hydrogen, (E)-3-[4-(2-pyrimidinyl)phenyl]-2-propenyl, (E)-3-[1-(2-pyrazinyl)-imidazol-4-yl]-2-propenyl, (E)-3-(4-isoquinolinyl)-2-propenyl, (E)-3-[1-(2-pyrimidinyl)-1H-imidazol-4-yl]-2-propenyl, and (E)-3-[3-(2-pyrimidinyl)phenyl]-2-propenyl.

The following compounds of Formula I are still preferred embodiments of the present invention, wherein $R^3$ is hydrogen or $OR^4$, wherein $R^4$ is $C_{1-8}$ alkyl;
$R^7$ is hydrogen;
$R^8$ is ethyl; and
$R^1$ and $R^2$ are independently selected from hydrogen, substituted $C_1$–$C_8$-alkyl, optionally substituted —$CH_2C_2$–$C_8$-alkenyl, and substituted —$CH_2C_2$–$C_8$-alkynyl, wherein the substituents are selected from aryl, substituted aryl, heteroaryl, and substituted heteroaryl.

In particular, the following compounds are preferred embodiments of the present invention for such purposes:

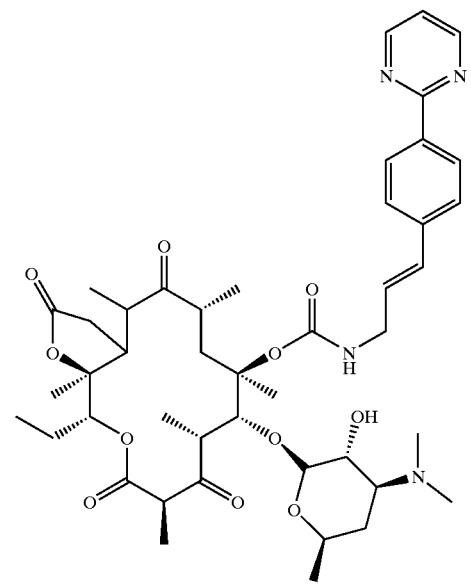

Compound 7 (Formula 1: $R_1$ is (E)-3-[4-(2-pyrimidinyl)phenyl]-2-propenyl, $R_2$ is H, $R_3$ is H, $R_7$ is H)

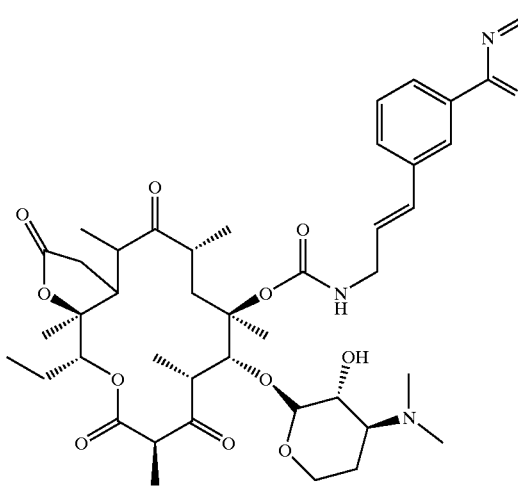

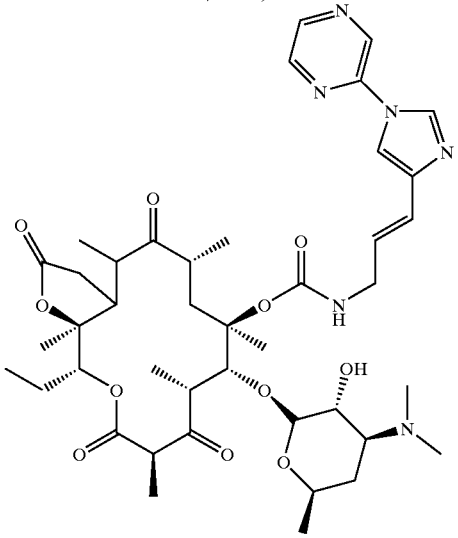

Compound 8 (Formula 1: $R_1$ is (E)-3-[3-(2-pyrimidinyl)phenyl)-2-propenyl, $R_2$ is H, $R_3$ is H, $R_7$ is H)

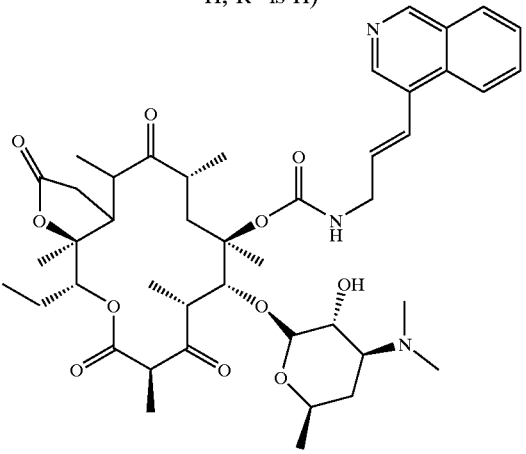

Compound 17 (Formula 1: $R_1$ is (E)-3-[1-(2-pyrazinyl)-imidazol-4-yl]-2-propenyl, $R_2$ is H, R is H, $R^7$ is H)

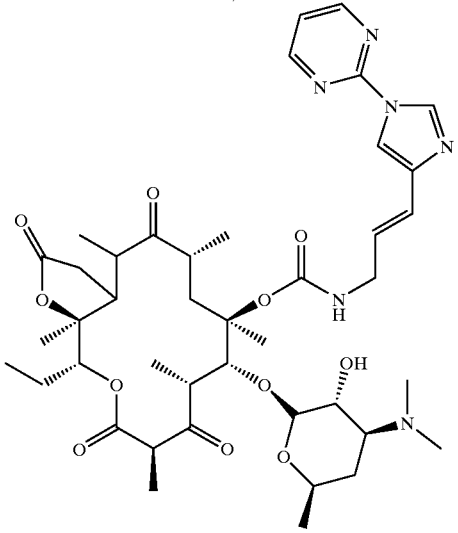

Compound 30 (Formula 1: $R_1$ is (E)-3-(4-isoquinolinyl)-2-propenyl, $R_2$ is H, $R_3$ is H, $R_7$ is H)

Compound 37 (Formula 1: $R_1$ is (E)-3-[1-(2-pyrimidinyl)-1H-imidazol-4-yl]-2-propenyl, $R_2$ is H, $R_3$ R is H, $R_7$ is H)

This invention also provides processes for preparing the instant compounds. The compounds of Formula I may be prepared from readily available starting materials such as erythromycin and erythromycin derivatives well known in the art. Outlined in Schemes 1 through 4 are representative procedures to prepare the compounds of the instant invention. Schemes 5 through 9 depict procedures to prepare key intermediates useful in the synthesis of compounds of the instant invention.

Scheme 1

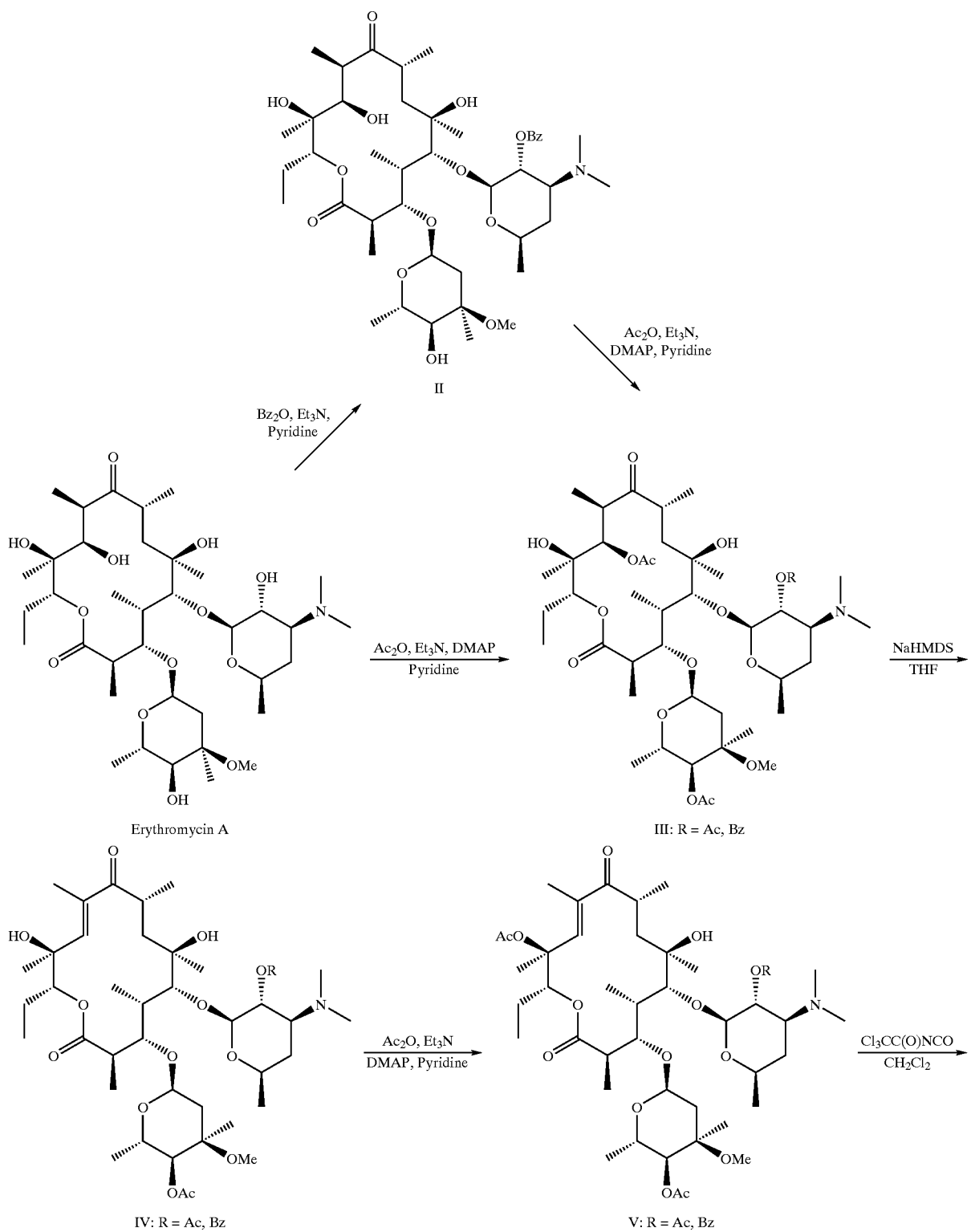

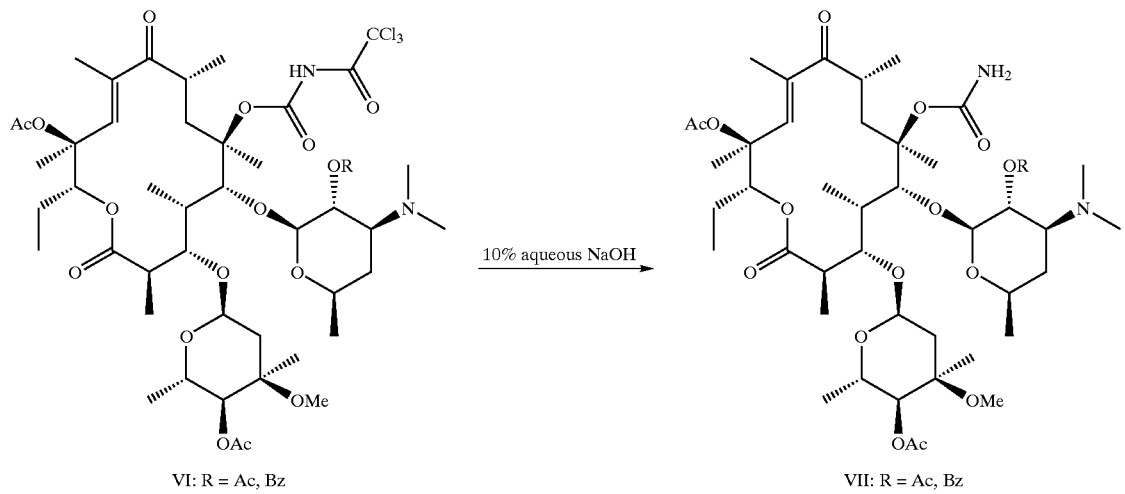

VI: R = Ac, Bz

VII: R = Ac, Bz

Scheme 1 illustrates the method of synthesis of the 2',4", 12-triacetyl-6-carbamyl-10,11-anhydroerythromycin A (VII: R=Ac) and 4",12-diacetyl-2'-benzoyl-6-carbamyl-10, 11-anhydroerythromycin A (VII: R=Bz) precursors to the compounds of the invention. Erythromycin A is treated with benzoic anhydride in the presence of a tertiary amine base, such as triethylamine, diisopropylethylamine, or pyridine, in a suitable solvent such as methylene chloride, chloroform, or THF (tetrahydrofuran) at a temperature ranging from −20° C. to 37° C. for 2 to 72 hours to afford 2'-benzoylerythromycin A (II). The diacetyl derivative (III: R=Bz) can be obtained by treatment of II with acetic anhydride in the presence of a tertiary amine base, such as pyridine, triethylamine, or diisopropylethylamine, and an acylation catalyst, such as DMAP (4-(dimethylamino) pyridine), in a suitable solvent such as methylene chloride, chloroform, or THF at a temperature ranging from −20° C. to 37° C. for 2 to 72 hours. Alternatively, the triacetyl derivative (III: R=Ac) may be obtained directly from erythromycin A by treatment with acetic anhydride in the presence of a tertiary amine base, such as triethylamine, diisopropylethylamine, or pyridine, and an acylation catalyst, such as DMAP, in a suitable solvent such as methylene chloride, chloroform, or THF at a temperature ranging from −20° C. to 37° C. for 2 to 72 hours. The 10,11-anhydro derivative (IV) can be readily obtained by treatment of III with a base in an inert solvent such as THF, dioxane DME (1,2-dimethoxyethane), or DMF (dimethylformamide) at a temperature ranging from −78° C. to 80° C. for 1 to 24 hours. Suitable bases to effect the elimination include, but are not limited to, sodium hexamethyldisilazide, potassium hexamethyldisilazide, LDA (lithium diisopropylamide), lithium tetramethylpiperidide, DBU (1,8-diazabicyclo[5.4.0]unded-7-ene), and tetramethylguanidine. It will be apparent to one skilled in the art that alternative methods for synthesis of 2',4"-diacetyl-10,11-anhydroerythromycin A are available, including conversion of erythromycin A to the 11,12-cyclic carbonate derivative with ethylene carbonate, followed by elimination with tetramethylguanidine, as described in Hauske, J. R. and Kostek, G., *J. Org. Chem.* 1982, 47, 1595.

Protection of the 2' and 4"-hydroxyl groups can then be readily accomplished with acetic anhydride in the presence of a tertiary amine base. Similarly, access to 4"-acetyl-2'-benzoyl-10,11-anhydroerythromycin A from 10,11-anhydroerythromycin A could be accomplished through selective protection of the 2'-hydroxyl group as the benzoate derivative with benzoic anhydride in the presence of a tertiary amine base or alkali metal carbonate, followed by acetylation of the 4"-hydroxyl group with acetic anhydride in the presence of pyridine. Alternative protecting group strategies also could be envisaged, in which the 2'- and 4"-hydroxyl groups are differentially protected with acetyl, propionyl, benzoyl, formyl, benzyloxycarbonyl, or trialkyl-silyl groups.

Once the suitably protected 10,11-anhydro derivative is obtained, acetylation of the 12-hydroxyl group to afford compound V can be accomplished by treatment with acetic anhydride in pyridine in the presence of a tertiary amine base, such as triethylamine or diisopropylethylamine, and an acylation catalyst, such as DMAP, at a temperature ranging from −20° C. to 80° C. for 2 to 72 hours. A suitable co-solvent, such as methylene chloride, chloroform, or THF may optionally be employed. Derivatization of the remaining tertiary hydroxy group can be carried out by treatment with trichloroacetylisocyanate in an inert solvent, such as methylene chloride, chloroform, or THF at a temperature ranging from −20° C. to 37° C. for 1–24 hours to yield the N-trichloroacetylcarbamate (VI). The N-trichloroacetylcarbamate functionality can be hydrolyzed to the corresponding primary carbamate (VII) by treatment with a suitable base, such as 10% sodium hydroxide, in a biphasic solvent system, such as ethyl acetate/water, methylene chloride/water, and the like for 1–24 hours at a temperature ranging from 20° C. to 80° C. Alternative bases may likewise be used to effect this conversion, such as potassium hydroxide, sodium carbonate, potassium carbonate, or a tertiary amine base, such as triethylamine, in an aqueous solvent mixture.

Scheme 2

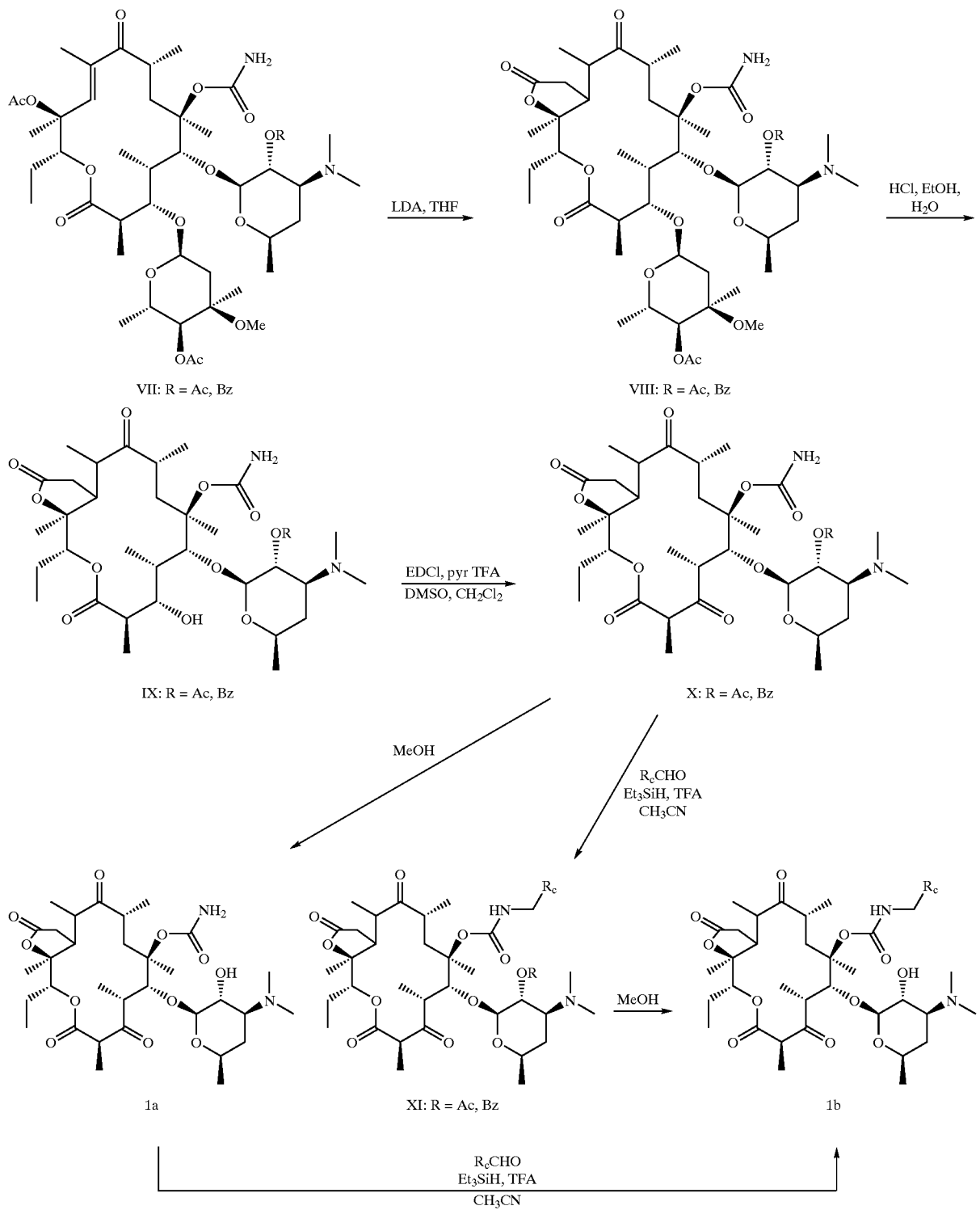

Scheme 2 depicts the synthesis of compounds of the instant invention represented by Formulae 1a and 1b, wherein RCCHO is an aldehyde ($R_c$ may be a member of the group including, but not limited to, hydrogen, alkyl, alkenyl, alkynyl, cycloalkyl, aryl, heteroaryl, heterocyclo, arylalkenyl, arylalkynyl, aralkyl, heteroarylalkenyl, heteroarylalkynyl, heteroarylalkyl, heterocycloalkenyl, heterocycloalkynyl, and heterocycloalkyl). The γ-lactone derivative (VIII) can be obtained by reaction of compound VII with a base in an inert solvent such as THF, dioxane, or DME at a temperature ranging from −78° C. to 20° C. for 1–24 hours. Suitable bases to effect this conversion include, but are not limited to, LDA, lithium tetramethylpiperidide, sodium hexamethyldisilazide, and potassium hexamethyldisilazide. It will be recognized by one skilled in the art that in the conversion of VII to VIII two new stereocenters are formed, and consequently VIII may exist as a mixture of diastereoisomers. These stereoisomers may be separated at this stage by a suitable chromatographic method, such as silica gel column chromatography or High Performance Liquid Chromatography (HPLC), or the mixture of stereoisomers may be carried on through the synthetic sequence, and optionally separated at a later step. Selective removal of the cladinose sugar can be accomplished by reaction of VIII with an acid, such as hydrochloric, sulfuric, chloroacetic, and trifluoroacetic, in the presence of alcohol and water to afford IX. Reaction time is typically 0.5–72 hours at a temperature ranging from −10° C. to 37° C. Oxidation of the 3-hydroxy group of IX to yield compound X can be effected with DMSO (dimethylsulfoxide) and a carbodiimide, such as EDCl (1-ethyl-3-(3-dimethylaminopropyl)carbodiimide), in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Removal of the 2'-acetyl group of compound X is readily accomplished by transesterification with methanol for 2–48 hours at a temperature ranging from −20° C. to 65° C. to yield compound 1a. If the 2'-benzoyl group is optionally employed as the protecting group in compound X, its removal can be readily accomplished by transesterification with methanol for 2–72 hours at a temperature ranging from 20° C. to 65° C. to yield compound 1a. Alternate methods for deprotection of the 2'-acetyl or 2'-benzoyl group include hydrolysis in the presence of an alkali metal hydroxide or an alkali metal carbonate, such as sodium hydroxide or potassium carbonate, or ammonolysis with ammonia in methanol. Compounds of formula XI can be obtained by selective alkylation of the primary carbamate of X with a suitably substituted aldehyde or acetal in the presence of a reducing agent and acid. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Compounds of formula 1b can then be obtained by removal of the 2'-acetyl or 2'-benzoyl group of compound XI, as described above for the conversion of X to 1a. Alternatively, compounds of formula 1b can be accessed directly from compounds of formula 1a by selective alkylation of the primary carbamate with a suitably substituted aldehyde in the presence of a reducing agent and acid, as described above for the conversion of X to XI.

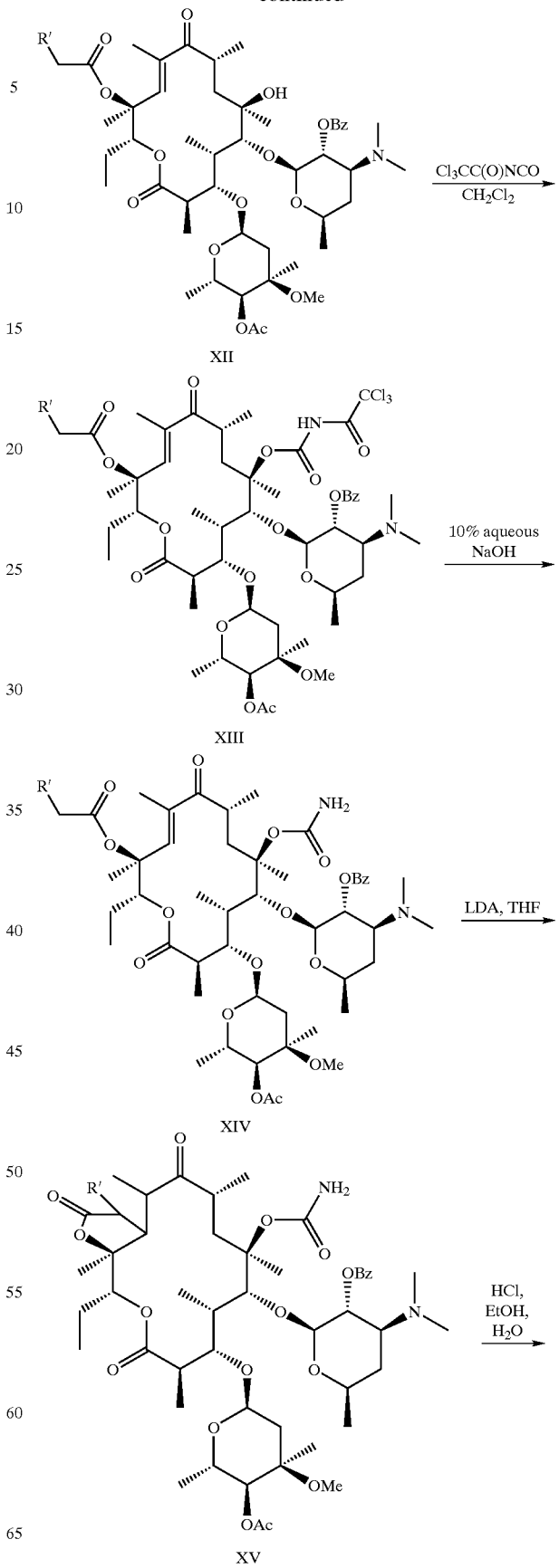

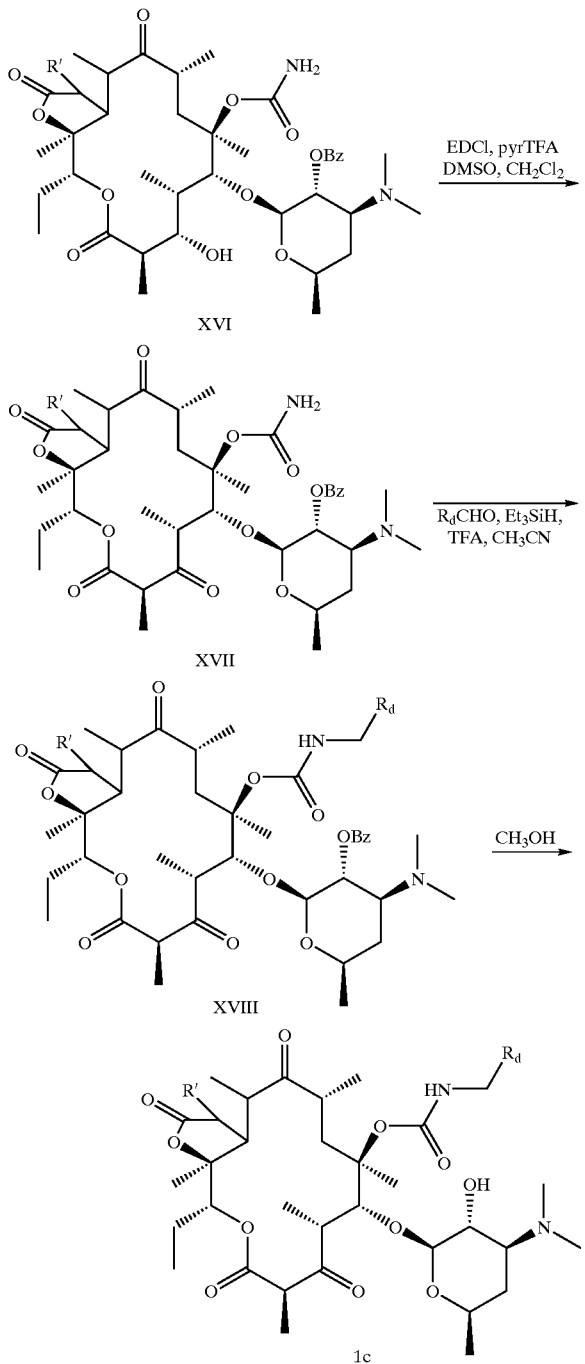

to afford compound XII. Alternative methods may also be employed to acylate the 12-hydroxy group, including reaction of compound IV with a pre-formed active ester derivative of the carboxylic acid, in the presence of an acylation catalyst, such as DMAP, in an inert solvent such as methylene chloride, chloroform, THF, or DMF. Suitable active ester derivatives include, but are not limited to, pentafluorophenyl, p-nitrophenyl, N-hydroxysuccinimide, and 3-hydroxy-3,4-dihydro-4-oxo-benzotriazine esters.

Derivatization of the remaining tertiary hydroxy group can be carried out by treatment with trichloroacetylisocyanate in an inert solvent, such as methylene chloride, chloroform, or THF at a temperature ranging from −20° C. to 37° C. for 1–24 hours to yield the N-trichloroacetylcarbamate (XIII). The N-trichloroacetylcarbamate functionality can be hydrolyzed to the corresponding primary carbamate (XIV) by treatment with a suitable base, such as 10% sodium hydroxide, in a biphasic solvent system, such as ethyl acetate/water, methylene chloride/water, and the like for 1–24 hours at a temperature ranging from 20° C. to 80° C. Alternative bases may likewise be used to effect this conversion, such as potassium hydroxide, sodium carbonate, potassium carbonate, or a tertiary amine base, such as triethylamine, in an aqueous solvent mixture.

The γ-lactone derivative (XV) can be obtained by reaction of compound XIV with a base in an inert solvent such as THF, dioxane, or DME at a temperature ranging from −78° C. to 20° C. for 1–24 hours. Suitable bases to effect this conversion include, but are not limited to, LDA, lithium tetramethylpiperidide, sodium hexamethyldisilazide, and potassium hexamethyldisilazide. It will be recognized by one skilled in the art that in the conversion of XIV to XV three new stereocenters are formed, and consequently XV may exist as a mixture of diastereoisomers. These stereoisomers may be separated at this stage by a suitable chromatographic method, such as silica gel column chromatography or HPLC, or the mixture of stereoisomers may be carried on through the synthetic sequence, and optionally separated at a later step. Selective removal of the cladinose sugar can be accomplished by reaction of XV with an acid, such as hydrochloric, sulfuric, chloroacetic, and trifluoroacetic, in the presence of alcohol and water to afford XVI. Reaction time is typically 0.5–72 hours at a temperature ranging from −10° C. to 37° C. Oxidation of the 3-hydroxy group of XVI to yield compound XVII can be effected with DMSO and a carbodiimide, such as EDCI, in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Compounds of formula XVIII can be obtained by selective alkylation of the primary carbamate of XVII with a suitably substituted aldehyde or acetal in the presence of a reducing agent and acid. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Compounds of formula 1c can then be obtained by transesterification of the 2'-benzoyl group of Scheme 3 depicts the synthesis of compounds of the instant invention of formula 1c, which contain a substituent (R') on the γ-lactone ring. As shown before, $R_dCHO$ is a suitably substituted aldehyde ($R_d$ may be a member of the group including, but not limited to, hydrogen, alkyl, alkenyl, alkynyl, cycloalkyl, aryl, heteroaryl, heterocyclo, arylalkenyl, arylalkynyl, aralkyl, heteroarylalkenyl, heteroarylalkynyl, heteroarylalkyl, heterocycloalkenyl, heterocycloalkynyl, and heterocycloalkyl). Compound IV' is treated with a suitably substituted carboxylic acid derivative in the presence of a coupling reagent, such as DCC, and an acylation catalyst, such as DMAP, in a suitable solvent such as pyridine, methylene chloride, chloroform, or THF at a temperature ranging from −20° C. to 62° C. for 2–72 hours compound XVIII with methanol for 2–72 hours at a temperature ranging from 20° C. to 65° C. The final two steps of Scheme 3 may be conducted in reverse order in a manner analogous to Scheme 2 to provide compounds of the instant invention of formula 1c.
Scheme 4
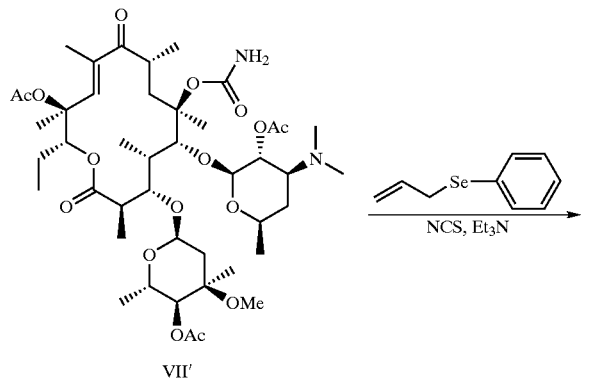
VII′
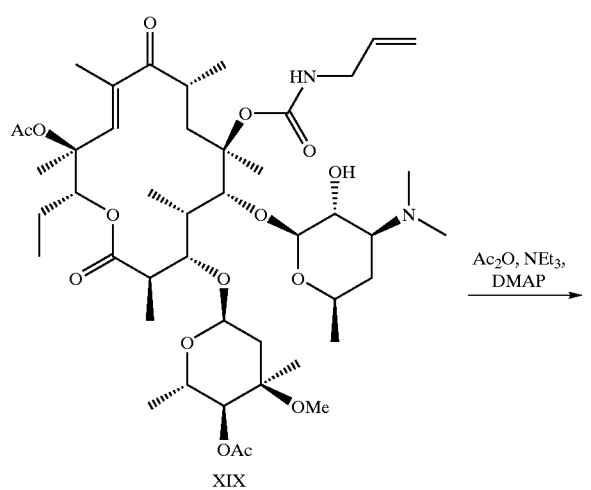
XIX
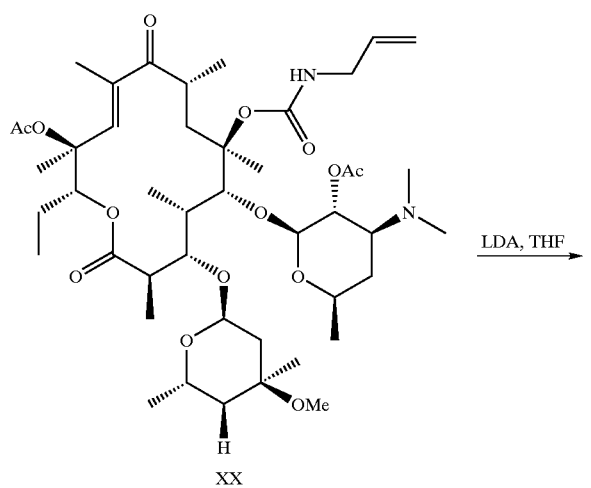
XX
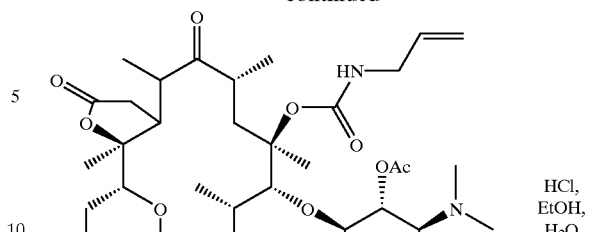
XXI
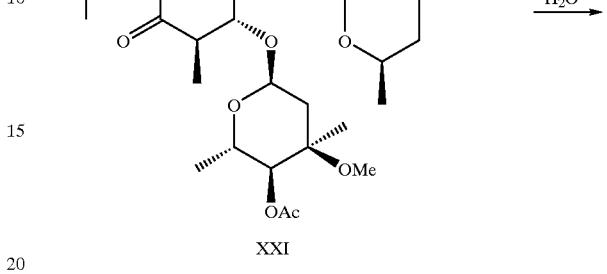
XXII
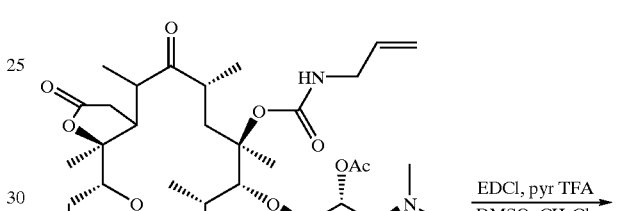
XXIII
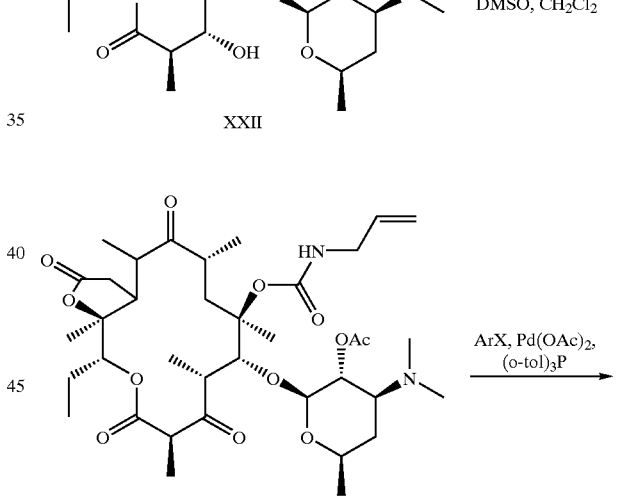
1d
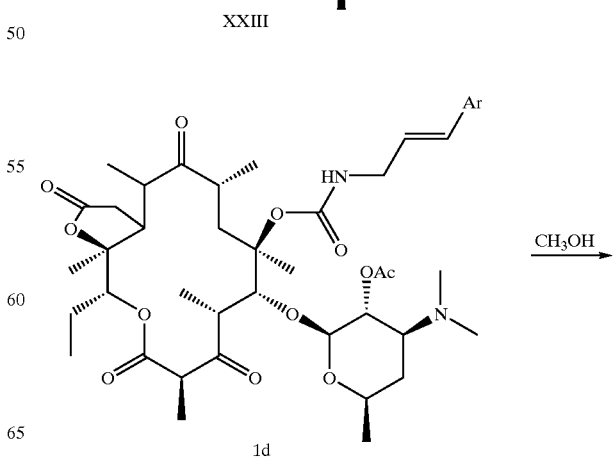

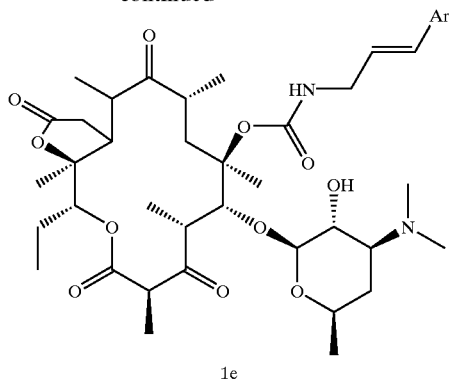

1e

Scheme 4 depicts the synthesis of compounds of the instant invention of formulae 1d and 1e. In compounds of formula 1e, Ar is aryl, substituted aryl, heteroaryl, or substituted heteroaryl. Compound VII' is treated with allyl phenyl selenide in the presence of a suitable oxidizing agent, such as N-chlorosuccinimide, and a tertiary amine base, such as triethylamine or diisopropylethylamine, in a suitable nucleophilic solvent, such as methanol, at −20° C. to 65° C. for 2 to 48 hours to afford the N-allyl carbamate derivative (XIX). Under the reaction conditions, the 2'-acetoxy group undergoes methanolysis to yield the corresponding hydroxyl. Alternate reaction conditions may likewise be used to effect the conversion of VII' to XIX, such as reaction of compound VII' with a suitable allylating agent, such as t-butyl allyl carbonate, in the presence of a transition metal catalyst, such as tris(benzylideneacetone)dipalladium, and a suitable phosphine ligand, such as 1,4-bis(diphenylphosphino)butane, in an inert solvent, such as THF (see, for example, WO 00/75156). Reprotection of the 2'-hydroxyl group to give XX can be carried out by treatment with acetic anhydride in the presence of a tertiary amine base, such as triethylamine, diisopropylethylamine, or pyridine, and optionally an acylation catalyst, such as DMAP, in a suitable solvent such as methylene chloride, chloroform or THF at a temperature ranging from −20° C. to 37° C. for 2 to 48 hours. The γ-lactone derivative (XXI) can be obtained by reaction of compound XX with a base in an inert solvent such as THF, dioxane, or DME at a temperature ranging from −78° C. to 20° C. for 1–24 hours. Suitable bases to effect this conversion include, but are not limited to, LDA, lithium tetramethylpiperidide, sodium hexamethyldisilazide, and potassium hexamethyldisilazide. It will be recognized by one skilled in the art that in the conversion of XX to XXI two new stereocenters are formed, and consequently XXI may exist as a mixture of diastereoisomers. These stereoisomers may be separated at this stage by a suitable chromatographic method, such as silica gel column chromatography or HPLC, or the mixture of stereoisomers may be carried on through the synthetic sequence, and optionally separated at a later step. Selective removal of the cladinose sugar can be accomplished by reaction of XXI with an acid, such as hydrochloric, sulfuric, chloroacetic, and trifluoroacetic, in the presence of alcohol and water to afford XXII. Reaction time is typically 0.5–72 hours at a temperature ranging from −10° C. to 37° C. Oxidation of the 3-hydroxy group of XXII to yield compound XXIII can be effected with DMSO and a carbodiimide, such as EDCI, in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Reaction of N-allyl carbamate (XXIII) with an aryl halide, a substituted aryl halide, a heteroaryl halide, or a substituted heteroaryl halide under Heck conditions with Pd(II) or Pd(0), a phosphine ligand, and a tertiary amine or inorganic base affords compounds of the instant invention 1d. Removal of the 2'-acetyl group of compound 1d is readily accomplished by transesterification with methanol for 2–48 hours at a temperature ranging from −20° C. to 65° C. to yield compounds of the instant invention 1e.

Scheme 5

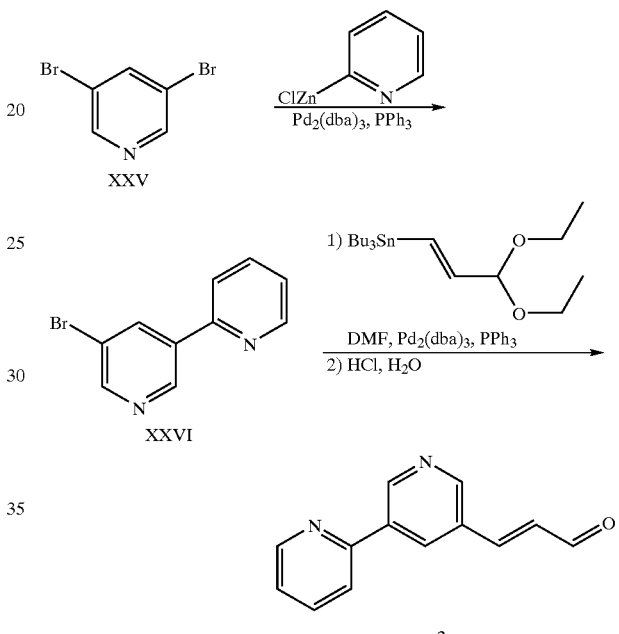

Scheme 5 depicts the synthesis of (E)-3-[5-(2-pyridinyl)-pyridin-3-yl]-2-propenal used in the preparation of Compound 11 and Compound 12). Reaction of 3,5-dibromopyridine (XXV) with chloro-2-pyridinylzinc under palladium catalysis conditions, in this case tris(benzylideneacetone)dipalladium and triphenylphosphine, in THF for 4 to 48 hours at 25° C. to 62° C. affords 3-bromo-5-(2-pyridinyl)pyridine (XXVI). Reaction of XXVI with tributyl[(1E)-3,3-diethoxy-1-propenyl]stannane (prepared as described in Parrain, J. L., Duchene, A., and Quintard, J. P., *J. Chem. Soc., Perkin Trans.* 1, 1990, 187), catalytic tris(benzylideneacetone)dipalladium and triphenylphosphine in DMF for 4 to 48 hours at 25° C. to 80° C., followed by hydrolysis with dilute hydrochloric acid for 15 minutes to 2 hours yields the desired aldehyde 2a.

Scheme 6

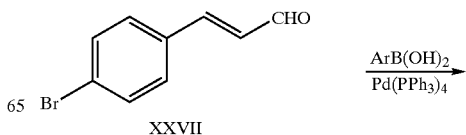

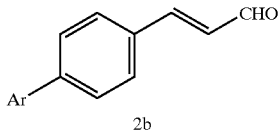

Scheme 6 illustrates the synthesis of certain of the aldehydes (2b) used in the preparation of compounds of the invention. Reaction of a bromocinnamaldehyde derivative (XXVII) with an aryl boronic acid to give the biaryl derivative (2b) is conducted under typical Suzuki coupling conditions, i.e., in the presence of a Pd⁰ catalyst, typically palladium tetrakistriphenylphosphine, and a base, typically sodium carbonate, potassium carbonate, potassium bicarbonate, potassium phosphate, or triethylamine in a suitable solvent, such as toluene, ethanol, methanol, DME, or THF. Reaction time is typically 2 to 48 hours at a temperature ranging from 20° C. to 110° C. Aryl iodides and aryl triflates are also suitable substrates for this conversion.

Reaction of 3-bromopyridine with propargyl alcohol under typical Sonogashira coupling conditions, i.e., in the presence of a Pd⁰ or Pd$^{II}$ catalyst, typically bis(acetonitrile) dichloropalladium (II), and an amine base, such as diisopropylethylamine, with a catalytic amount of copper(I) salt, typically copper iodide, and a phosphine ligand, such as tri-t-butylphosphine in a suitable solvent, such as THF, affords the desired 3-(3-pyridinyl)-2-propynal (XXXI). Reaction time is typically 2 to 72 hours at a temperature ranging from −20° C. to 62° C. Oxidation of the alcohol derivative (XXXI) to the corresponding aldehyde (2d) can be readily carried out by treatment with manganese dioxide in a suitable solvent, such as methylene chloride, for 2 to 48 hours, at a temperature ranging from 0° C. to 37° C. Alternative reagents for oxidation of the alcohol can be contemplated, such as N-chlorosuccinimide and dimethylsulfide complex followed by a tertiary amine base, Dess-Martin periodinane, oxalyl chloride/DMSO followed by treatment with a tertiary amine base, or chromium-based oxidants, such as pyridinium chlorochromate or pyridinium dichromate.

Scheme 7

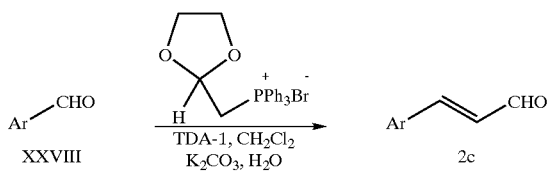

Scheme 7 illustrates a method of synthesis of certain of the aldehydes (2c) used in the preparation of compounds of the invention. Wittig-type reaction of an aromatic aldehyde (XXVIII) with 1,3-dioxolan-2-yl-methyltriphenylphosphonium bromide under phase transfer conditions in a biphasic solvent system in the presence of an inorganic base, such as potassium carbonate, affords the corresponding vinylogous aldehyde (2c). Th reaction is typically run from 2 to 48 hours at temperatures ranging from 0° C. to 37° C. The method is more fully described in Daubresse, N., Francesch, C. and Rolando, C., *Tetrahedron*, 1998, 54, 10761.

Scheme 8

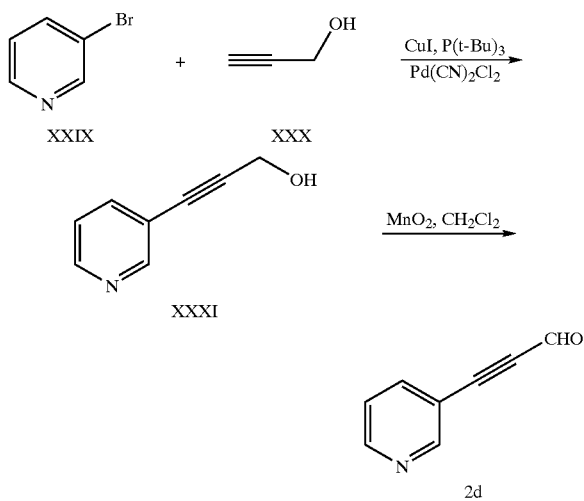

Scheme 8 depicts the synthesis of 3-(3-pyridinyl)-2-propynal (2d) used in the preparation of Compound 18.

Scheme 9

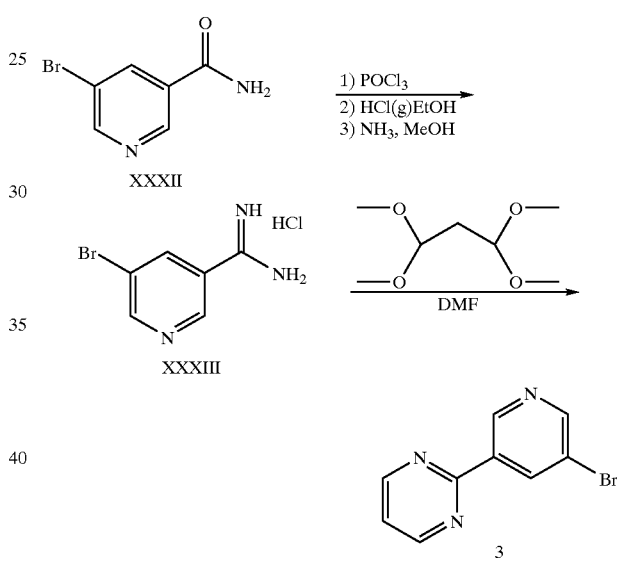

Scheme 9 illustrates the synthesis of 3-bromo-5-(2-pyrimidinyl)pyridine (3) used in the preparation of Compound 40. Reaction of 5-bromo-3-pyridine carboxamide (XXXII) with phosphorus oxychloride at temperatures ranging from 20° C. to 106° C. for 2 to 48 hours affords the corresponding nitrile. The nitrile is converted to the corresponding amidine (XXXIII) by first treating with gaseous hydrogen chloride and ethanol to obtain the imidate, and then reacting the imidate with ammonia, typically in an alcoholic solvent, such as methanol. The amidine may be isolated as the free base or an acid addition salt, preferably the hydrochlride salt. Reaction of the amidine hydrochloride (XXXIII) with 1,1,3,3-tetramethoxypropane in a suitable solvent, such as dimethylformamide or N-methylpyrrolidinone, affords the desired 3-bromo-5-(2-pyrimidinyl)pyridine (3). Typically the reaction is carried out at temperatures ranging from 20° C. to 110° C. for 2 to 72 hours.

When the aldehydes, acetals, or aryl halides used in the preparation of compounds XI, XVIII, and XXIII are not commercially available, they can be obtained by conventional synthetic procedures, in accordance with literature precedent, from readily accessible starting materials using standard reagents and reaction conditions. Exemplary syntheses of several of the aldehydes used in the preparation of XI, XVIII, and XXIII are presented hereinafter as reference examples.

Compounds of the invention wherein $R^7$ is a hydroxy protecting group other than acyl may be prepared in methods analogous to those shown in the above schemes with appropriate reagents that are either commercially available or may be made by known methods.

Compounds of the invention wherein the substituent at 13-position (i.e., $R^8$) is a group other than ethyl may be prepared beginning with modified erythromycin derivatives as starting materials, such as those described in WO 99/35157, WO 00/62783, WO 00/63224, and WO 00/63225.

These compounds have antimicrobial activity against susceptible and drug resistant Gram positive and Gram negative bacteria. In particular, they are useful as broad spectrum antibacterial agents for the treatment of bacterial infections in humans and animals. These compounds are particularly activity against *S. aureus, S. epidermidis, S. pneumoniae, S. pyogenes*, Enterococci, *Moraxella catarrhalis* and *H. influenzae*. These compounds are particularly useful in the treatment of community-acquired pneumonia, upper and lower respiratory tract infections, skin and soft tissue infections, meningitis, hospital-acquired lung infections, and bone and joint infections.

Minimal inhibitory concentration (MIC) has been an indicator of in vitro antibacterial activity widely used in the art. The in vitro antimicrobial activity of the compounds was determined by the microdilution broth method following the test method from the National Committee for Clinical Laboratory Standards (NCCLS). This method is described in the NCCLS Document M7-A4, Vol.17, No.2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities depending on the organism tested.

Table 1 below sets forth the biological activity (MIC, µg/mL) of some compounds of the present invention.

TABLE 1

MIC Values (µg/mL) of Some Compounds of Formula I
(A: *E. coli* OC2605; B: *S. aureus* ATCC29213; C: *E. faecalis* ATCC29212; D: *S. pneumoniae* ATCC49619; E: *H. influenzae* ATCC49247)

| | MIC (µg/mL) | | | | |
|---|---|---|---|---|---|
| No. | A | B | C | D | E |
| 1 | >16 | 8 | 2 | 0.5 | >16 |
| 2 | >16 | 1 | 0.12 | 0.06 | 16 |
| 3 | >16 | 1 | 0.25 | 0.06 | 8 |
| 4 | >16 | >16 | 8 | 1 | >16 |
| 5 | 16 | 0.5 | 0.06 | 0.03 | 16 |
| 6 | >16 | 1 | 1 | 0.25 | 8 |
| 7 | >16 | 0.25 | 0.12 | 0.06 | 8 |
| 8 | >16 | 0.5 | 0.12 | 0.06 | 2 |
| 9 | >16 | 0.5 | 0.25 | 0.06 | 8 |
| 10 | >16 | 1 | 0.5 | 0.12 | 8 |
| 11 | >16 | 0.5 | 0.12 | 0.06 | 4 |
| 12 | >16 | 2 | 0.5 | 0.12 | 16 |
| 13 | >16 | 1 | 0.25 | 0.06 | 4 |
| 14 | >16 | 2 | 0.5 | 0.12 | 8 |
| 15 | >16 | 1 | 0.25 | 0.12 | 8 |
| 16 | 16 | 0.5 | 0.25 | 0.06 | 4 |
| 17 | >16 | 0.5 | 0.12 | 0.06 | 4 |
| 18 | >16 | 2 | 0.5 | 0.12 | 8 |
| 19 | >16 | 16 | 1 | 0.25 | >16 |
| 20 | >16 | 2 | 0.5 | 0.12 | 16 |
| 21 | >16 | 2 | 1 | 0.25 | 8 |
| 22 | 16 | 1 | 0.25 | 0.06 | 4 |
| 23 | >16 | 8 | 2 | 2 | >16 |
| 24 | >16 | 0.5 | 0.25 | 0.06 | 4 |
| 25 | >16 | 0.5 | 0.25 | 0.06 | 4 |
| 26 | >16 | 1 | 0.12 | 0.06 | 8 |
| 27 | 16 | 0.5 | 0.06 | 0.03 | 1 |
| 28 | >16 | 2 | 0.5 | 0.12 | 8 |
| 29 | >16 | 0.5 | 0.25 | 0.06 | 2 |
| 30 | 16 | 0.25 | 0.12 | | 2 |
| 31 | 16 | 0.25 | 0.06 | 0.03 | >16 |
| 32 | >16 | 0.5 | 0.25 | 0.06 | 8 |
| 33 | >16 | 2 | 0.5 | 0.12 | 8 |
| 34 | >16 | 0.5 | 0.12 | 0.06 | 2 |
| 35 | >16 | 0.5 | 0.25 | 0.12 | 4 |
| 36 | >16 | 4 | 1 | 0.25 | 16 |
| 37 | >16 | 0.5 | 0.12 | 0.03 | 4 |
| 38 | >16 | 0.5 | 0.12 | 0.03 | 2 |
| 39 | 16 | 0.5 | 0.12 | 0.03 | 4 |
| 40 | 16 | 0.25 | 0.12 | 0.03 | 1 |

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT (2,6-di-tert-butyl-4-methylphenol) and BHA (2-tert-butyl-4-methoxyphenol).

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, which may be given in divided doses two to four times a day, or in sustained release form. For most large mammals the total daily dosage is from about 0.07 g to 7.0 g, preferably from about 100 mg to 2000 mg. Dosage forms suitable for internal use comprise from about 100 mg to 1200 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Compound 1 (Formula 1: $R_1$ is H, $R_2$ is H, $R_3$ is H, $R_7$ is H, $R_8$ is Ethyl)

A solution of the product of Reference Example 21 was dissolved in methanol (2 mL) and was stirred for 24 h. Purification by chromatography ($SiO_2$, 94:6:0.5 dichloromethane/methanol/conc. $NH_4OH$) yielded 13.4 mg (17%) of the title compound as a colorless foam. MS 642 $(M+H)^+$.

EXAMPLE 2

Compound 2 (Formula 1: $R_1$ is 4-(5-pyrimidinyl)-benzyl, $R_2$ is H, $R_3$ is H, $R_7$ is H, $R_8$ is ethyl)

A solution of the product of Reference Example 21 (50 mg, 0.073 mmol), triethylsilane (0.033 mL, 0.21 mmol), trifluoroacetic acid (0.016 mL, 0.21 mmol), and 4-(5-pyrimidinyl)-benzaldehyde (prepared as described in WO9736896; 39 mg, 0.21 mmol) in $CH_3CN$ (0.5 mL) was stirred at 25° C. for 36 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was stirred for 12 h. Purification by chromatography ($SiO_2$, 94:6:0.5 dichloromethane/methanol/conc. $NH_4OH$) yielded 1.5 mg (2.5%) of the title compound as a colorless foam. MS 810 $(M+H)^+$.

EXAMPLE 3

Compound 3 (Formula 1: $R_1$ is 6-quinolinylmethyl, $R_2$ is H, $R_3$ is H, $R_7$ is H, $R_8$ is ethyl)

A solution of the product of Reference Example 21 (50 mg, 0.073 mmol), triethylsilane (0.26 mL, 1.62 mmol), trifluoroacetic acid (0.13 mL, 1.62 mmol), and 6-quinolinecarboxaldehyde (171 mg, 1.08 mmol) in $CH_3CN$ (0.1 mL) was warmed to reflux for 18 h. The reaction mixture was allowed to cool to 25° C., diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was stirred for 12 h. Purification by chromatography ($SiO_2$, 94:6:0.5 dichloromethane/methanol/conc. $NH_4OH$) yielded 6.0 mg (11%) of the title compound as a green foam. MS 782 $(M+H)^+$.

EXAMPLE 4

Compound 4 (Formula 1: $R_1$ is 4-carboxybenzyl, $R_2$ is H, $R_3$ is H. $R_7$ is H, $R_8$ is Ethyl)

A solution of the product of Reference Example 21 (100 mg, 0.146 mmol), triethylsilane (0.116 mL, 0.73 mmol), trifluoroacetic acid (0.060 mL, 0.73 mmol), and 4-formylbenzoic acid (109 mg, 0.73 mmol) in $CH_3CN$ (1.0 mL) was warmed to reflux for 2.5 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was stirred for 12 h. Purification by chromatography (SiO2, 94:6:0.5 dichloromethane/methanol/conc. NH$_4$OH) yielded 26.8 mg (24%) of the title compound as a colorless foam. MS 775 (M+H)$^+$.

EXAMPLE 5

Compound 5 (Formula 1: R$_1$ is (E)-3-(3-quinolinyl)-2-propenyl, R$_2$ is H, R$_3$ is H, R$_7$ is H, R$_8$ is Ethyl)

A solution of the product of Reference Example 21 (82 mg, 0.12 mmol), triethylsilane (0.100 mL, 0.60 mmol), trifluoroacetic acid (0.060 mL, 0.60 mmol), and (E)-3-(3-quinolinyl)-2-propenal (prepared as described in WO9902524; 110 mg, 0.60 mmol) in CH$_3$CN (0.4 mL) was stirred for 24 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was stirred for 12 h. Purification by chromatography (SiO$_2$, 94:6:0.5 dichloromethane/methanol/conc. NH$_4$OH) yielded 14.8 mg (15%) of the title compound as a colorless foam. MS 808 (M+H)$^+$.

EXAMPLE 6

Compound 6 (Formula 1: R$_1$ is (E)-3-[4-(2-pyridinyl)phenyl]-2-propenyl, R$_2$ is H, R$_3$ is Methoxy, R$_7$ is H, R$_8$ is Ethyl)

A solution of the product of Reference Example 20 (45 mg, 0.058 mmol), triethylsilane (0.063 mL, 0.40 mmol), trifluoroacetic acid (0.038 mL, 0.40 mmol), and (E)-3-[4-(2-pyridinyl)phenyl]-2-propenal (product of Reference Example 31; 61 mg, 0.29 mmol) in CH$_3$CN (0.5 mL) was stirred for 24 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 6.3 mg (15%) of the title compound as a colorless foam. MS 865 (M+H)$^+$.

EXAMPLE 7

Compound 7 (Formula 1: R$_1$ is (E)-3-[4-(2-pyridinyl)phenyl]-2-propenyl, R$_2$ is H, R$_3$ is H, R$_7$ is H, R$_8$ is Ethyl)

A solution of the product of Reference Example 21 (75 mg, 0.110 mmol), triethylsilane (0.090 mL, 0.55 mmol), trifluoroacetic acid (0.050 mL, 0.55 mmol), and (E)-3-[4-(2-pyridinyl)phenyl]-2-propenal (product of Reference Example 30; 116 mg, 0.55 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 13.5 mg (15%) of the title compound as a colorless foam. MS 835 (M+H)$^+$.

EXAMPLE 8

Compound 8 (Formula 1: R$_1$ is (E)-3-[3-(2-pyrimidinyl)phenyl)-2-propenyl, R$_2$ is H, R$_3$ is H, R$_7$ is H, R$_8$ is Ethyl)

A solution of the product of Reference Example 18 (100 mg, 0.130 mmol), triethylsilane (0.120 mL, 0.78 mmol), trifluoroacetic acid (0.080 mL, 0.78 mmol), and (E)-3-[3-(2-pyrimidinyl)phenyl)-2-propenal (product of Reference Example 37; 136 mg, 0.65 mmol) in CH$_3$CN (0.5 mL) was stirred for 48 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 10 mg (9%) of the title compound as a colorless foam. MS 835 (M+H)$^+$.

EXAMPLE 9

Compound 9 (Formula 1: R$_1$ is (E)-3-[4-(5-pyrimidinyl)phenyl]-2-propenyl, R$_2$ is H, R$_3$ is H, R$_7$ is H, R$_8$ is Ethyl)

A solution of the product of Reference Example 18 (48 mg, 0.065 mmol), triethylsilane (0.100 mL, 0.65 mmol), trifluoroacetic acid (0.060 mL, 0.65 mmol), and (E)-3-[4-(5-pyrimidinyl)phenyl]-2-propenal (product of Reference Example 33; 137 mg, 0.65 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 2.5 mg (5%) of the title compound as a colorless foam. MS 836 (M+H)$^+$.

EXAMPLE 10

Compound 10 (Formula 1: R$_1$ is (E)-3-(7-quinolinyl)-2-propenyl, R$_2$ is H, R$_3$ is Methoxy, R$_7$ is H, R$_8$ is Ethyl)

A solution of the product of Reference Example 20 (100 mg, 0.129 mmol), triethylsilane (0.103 mL, 0.65 mmol), trifluoroacetic acid (0.06 mL, 0.65 mmol), and (E)-3-(7-quinolinyl)-2-propenal (product of Reference Example 38; 119 mg, 0.65 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 1.5 mg (1.4%) of the title compound as a colorless foam. MS 839 (M+H)$^+$.

EXAMPLE 11

Compound 11 (Formula 1: R$_1$ is (E)-3-[5-(2-pyridinyl)-Pyridin-3-yl]-2-propenyl, R$_2$ is H, R$_3$ is H, R$_7$ is H, R$_8$ is Ethyl) and Compound 12 (Formula 1: R$_1$ is (E)-3-[5-(2-pyridinyl)-pyridin-3-yl]-2-propenyl, R$_2$ is (E)-3-[5-(2-pyridinyl)-pyridin-3-yl]-2-propenyl, R$_3$ is H, R$_7$ is H, R$_8$ is Ethyl)

A solution of the product of Reference Example 21 (75 mg, 0.110 mmol), triethylsilane (0.090 mL, 0.55 mmol), trifluoroacetic acid (0.050 mL, 0.55 mmol), and (E)-3-[5-(2-pyridinyl)-pyridin-3-yl]-2-propenal (product of Reference Example 41; 105 mg, 0.55 mmol) in CH$_3$CN (0.5 mL)

was stirred for 48 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 4.5 mg (5%) of the monoalkylated [MS 836 (M+H)+] and 2.4 mg (2%) of the dialkylated [MS 1030 (M+H)$^+$] compounds as colorless foams.

EXAMPLE 12

Compound 13 (Formula 1: R$_1$ is (E)-3-[3-(2-pyridinyl)phenyl]-2-propenyl, R$_2$ is H, R$_3$ is H, R$_7$ is H, R$_8$ is Ethyl)

A solution of the product of Reference Example 18 (118 mg, 0.159 mmol), triethylsilane (0.126 mL, 0.79 mmol), trifluoroacetic acid (0.125 mL, 0.79 mmol), and (E)-3-[3-(2-pyridinyl)phenyl]-2-propenal (product of Reference Example 36; 167 mg, 0.79 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 11 mg (8%) of the title compound as a colorless foam. MS 835 (M+H)$^+$.

EXAMPLE 13

Compound 14 (Formula 1: R$_1$ is (E)-3-(3-(3-pyridinyl)phenyl)-2-propenyl, R$_2$ is H, R$_3$ is H, R$_7$ is H, R$_8$ is Ethyl)

A solution of the product of Reference Example 18 (75 mg, 0.100 mmol), triethylsilane (0.083 mL, 0.54 mmol), trifluoroacetic acid (0.053 mL, 0.54 mmol), and (E)-3-(3-(3-pyridinyl)phenyl)-2-propenal (prepared as described in *Heterocycles* 1994, 38,1551; 113 mg, 0.54 mmol) in CH$_3$CN (0.5 mL) was stirred for 48 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 7.6 mg (9%) of the title compound as a colorless foam. MS 835 (M+H)$^+$.

EXAMPLE 14

Compound 15 (Formula 1: R$_1$ is (E)-3-[4-(2-pyridinyl)phenyl]-2-propenyl, R$_2$ is H, R$_3$ is H, R$_7$ is H, R$_8$ is Ethyl)

A solution of the product of Reference Example 18 (146 mg, 0.196 mmol), triethylsilane (0.150 mL, 0.98 mmol), trifluoroacetic acid (0.090 mL, 0.98 mmol), and (E)-3-[4-(2-pyridinyl)phenyl]-2-propenal (product of Reference Example 31; 204 mg, 0.98 mmol) in CH$_3$CN (0.5 mL) was stirred for 24 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 1.5 mg (0.9%) of the title compound as a colorless foam. MS 835 (M+H)$^+$.

EXAMPLE 15

Compound 16 (Formula 1: R$_1$ is (E)-3-[4-(1,3,4-triazol-1-yl)phenyl]-2-propenyl, R$_2$ is H, R$_3$ is H, R$_7$ is H, R$_8$ is Ethyl)

A solution of the product of Reference Example 18 (94 mg, 0.126 mmol), triethylsilane (0.126 mL, 0.79 mmol), trifluoroacetic acid (0.125 mL, 0.79 mmol), and (E)-3-[4-(1,3,4-triazol-1-yl)phenyl]-2-propenal (product of Reference Example 47;126 mg, 0.63 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 7.8 mg (8%) of the title compound as a colorless foam. MS 824 (M+H)$^+$.

EXAMPLE 16

Compound 17 (Formula 1: R$_1$ is (E)-3-[1-(2-pyrazinyl)-imidazol-4-yl]-2-propenyl, R$_2$ is H, R$_3$ is H, R$_7$ is H, R$_8$ is Ethyl)

A solution of the product of Reference Example 18 (100 mg, 0.134 mmol), triethylsilane (0.126 mL, 0.79 mmol), trifluoroacetic acid (0.125 mL, 0.79 mmol), and (E)-3-[1-(2-pyrazinyl)-imidazol-4-yl]-2-propenal (product of Reference Example 46; 134 mg, 0.67 mmol) in CH$_3$CN (0.5 mL) was stirred for 72 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 10.5 mg (10%) of the title compound as a colorless foam. MS 825 (M+H)$^+$.

EXAMPLE 17

Compound 18 (Formula 1: R$_1$ is 3-(3-pyridinyl)-2-propynyl R$_2$ is H, R$_3$ is H, R$_7$ is H, R$_8$ is Ethyl)

A solution of the product of Reference Example 18 (100 mg, 0.134 mmol), triethylsilane (0.126 mL, 0.79 mmol), trifluoroacetic acid (0.125 mL, 0.79 mmol), and 3-(3-pyridinyl)-2-propynal (product of Reference Example 42; 99.6 mg, 0.76 mmol) in CH$_3$CN (0.5 mL) was stirred for 36 h at 25° C. The reaction mixture was diluted with ethyl acetate (20 mL), washed with sat. aq. NaHCO$_3$ (20 mL) and brine (20 mL), dried (Na$_2$SO$_4$), and concentrated. The residue was dissolved in methanol (2 mL) and was warmed to reflux for 12 h, allowed to cool to 25° C., and concentrated. Purification by chromatography (SiO$_2$, 94:6:0.5 dichloromethane/methanol/conc. NH$_4$OH) yielded 4 mg (4%) of the title compound as a red foam. MS 756 (M+H)$^+$.

EXAMPLE 18

Compound 19 (Formula 1: R$_1$ is benzyl, R$_2$ is H, R$_3$ is H, R$_7$ is H, R$_8$ is Ethyl)

A solution of the product of Reference Example 21 (63 mg, 0.092 mmol), triethylsilane (0.029 mL, 0.184 mmol), trifluoroacetic acid (0.014 mL, 0.184 mmol), and benzaldehyde (0.045 mL, 0.46 mmol) in $CH_3CN$ (0.5 mL) was stirred at 25° C. for 18 h. The reaction mixture was diluted with ethyl acetate (30 mL), washed with sat. aq. $NaHCO_3$ (30 mL) and brine (30 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 6 mg (9%) of the title compound as a colorless solid. MS 732 $(M+H)^+$.

EXAMPLE 19

Compound 20 (Formula 1: $R_1$ is 4-bromobenzyl, $R_2$ is H, $R_3$ is H, $R_7$ is H, $R_8$ is Ethyl)

A solution of the product of Reference Example 21 (75 mg, 0.109 mmol), triethylsilane (0.035 mL, 0.219 mmol), trifluoroacetic acid (0.017 mL, 0.219 mmol), and 4-bromobenzaldehyde (101 mg, 0.547 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 6.5 mg (7.3%) of the title compound as a colorless solid. MS 811 $(M+H)^+$.

EXAMPLE 20

Compound 21 (Formula 1: $R_1$ is 4-[(E)-2-phenylethenyl]benzyl, $R_2$ is H, $R_3$ is H, $R_7$ is H, $R_8$ is Ethyl)

A solution of the product of Reference Example 21 (72.0 mg, 0.105 mmol), triethylsilane (0.034 mL, 0.210 mmol), trifluoroacetic acid (0.016 mL, 0.210 mmol), and 4-[(E)-2-phenylethenyl]benzaldehyde (109 mg, 0.527 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 42 mg (48%) of the title compound as a colorless solid. MS 834 $(M+H)^+$.

EXAMPLE 21

Compound 22 (Formula 1: $R_1$ is (E)-3-(4-bromophenyl)-2-propenyl, $R_2$ is H, $R_3$ is H, $R_7$ is H, $R_8$ is ethyl) and Compound 23 (Formula 1: $R_1$ is (E)-3-(4-bromophenyl)-2-propenyl, $R_2$ is (E)-3-(4-bromophenyl)-2-propenyl, $R_3$ is H, $R_7$ is H, $R_8$ is Ethyl)

A solution of the product of Reference Example 21 (72.0 mg, 0.105 mmol), triethylsilane (0.034 mL, 0.210 mmol), trifluoroacetic acid (0.016 mL, 0.210 mmol), and 4-bromocinnamaldehyde (prepared as described in *Tetrahedron* 1998, 54,10761; 112 mg, 0.527 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 32 mg (37%) of the monoalkylated compound as a colorless solid [MS 836 $(M+H)^+$] and 8.5 mg (8%) of the dialkylated compound [1030 $(M+H)^+$].

EXAMPLE 22

Compound 24 (Formula 1: $R_1$ is 3-quinolinylmethyl, $R_2$ is H, $R_3$ is H, $R_7$ is H, $R_8$ is Ethyl, 10β-epimer) and Compound 25 (Formula 1: $R_1$ is 3-quinolinylmethyl, $R_2$ is H, $R_3$ is H, $R_7$ is H, $R_8$ is ethyl, 10α-epimer)

A solution of the product of Reference Example 21 (65.0 mg, 0.95 mmol), triethylsilane (0.076 mL, 0.47 mmol), trifluoroacetic acid (0.037 mL, 0.47 mmol), and 3-quinolinecarboxaldehyde (149 mg, 0.95 mmol) in toluene (0.5 mL) was stirred at 105° C. for 10 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded the 10β-epimer [MS 783 $(M+H)^+$] (8.3 mg (11%) and the more polar 10α-epimer (6.8 mg (9%) [MS 783 $(M+H)^+$].

EXAMPLE 23

Compound 26 (Formula 1: $R_1$ is 4-(2-pyridinyl)benzyl, $R_2$ is H, $R_3$ is H, $R_7$ is H, $R_8$ is Ethyl)

A solution of the product of Reference Example 21 (52 mg, 0.076 mmol), triethylsilane (0.029 mL, 0.38 mmol), trifluoroacetic acid (0.016 mL, 0.38 mmol), and 4-(2-pyridinyl)benzaldehyde (139 mg, 0.76 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 5.3 mg (9%) of the title compound as a colorless solid. MS 808 $(M+H)^+$.

EXAMPLE 24

Compound 27 (Formula 1: R, is (E)-3-(6-quinolnyl)-2-propenyl, $R_2$ is H, $R_3$ is H, $R_7$ is H, $R_8$ is Ethyl)

A solution of the product of Reference Example 21 (65 mg, 0.095 mmol), triethylsilane (0.061 mL, 0.38 mmol), trifluoroacetic acid (0.0.29 mL, 0.38 mmol), and (E)-3-(6-quinolinyl)-2-propenal (product of Reference Example 29; 87 mg, 0.48 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was stirred for 12 h. Purification by chromatography ($SiO_2$, 94:6:0.5 dichloromethane/methanol/conc. $NH_4OH$) yielded 42.5 mg (56%) of the title compound. Recrystallization from $CH_2Cl_2$/hexanes afforded 10.4 mg as a tan solid. MS 808 $(M+H)^+$.

EXAMPLE 25

Compound 28 (Formula 1: $R_1$ is 2-quinolinylmethyl, $R_2$ is H, $R_3$ is H. $R_7$ is H, $R_8$ is Ethyl)

A solution of the product of Reference Example 21 (68 mg, 0.100 mmol), triethylsilane (0.127 mL, 0.797 mmol), trifluoroacetic acid (0.061 mL, 0.797 mmol), and 2-quinolinecarboxaldehyde (156 mg, 1.00 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was stirred for 12 h. Purification by chromatography ($SiO_2$, 94:6:0.5 dichloromethane/methanol/conc. $NH_4OH$) yielded 7.9 mg (10%) of the title compound as a colorless solid. MS 782 $(M+H)^+$.

EXAMPLE 26

Compound 29 (Formula 1: $R_1$ is (E)-3-[4-(2-pyridinyl)phenyl]-2-propenyl, $R_2$ is H, $R_3$ is H, $R_7$ is H, $R_8$ is Ethyl)

A solution of the product of Reference Example 21 (79 mg, 0.115 mmol), triethylsilane (0.074 mL, 0.462 mmol), trifluoroacetic acid (0.036 mL, 0.462 mmol), and (E)-3-[4-(2-pyridinyl)phenyl]-2-propenal (product of Reference Example 31; 121 mg, 0.578 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 19.6 mg (21%) of the title compound as a colorless solid. MS 835 $(M+H)^+$.

EXAMPLE 27

Compound 30 (Formula 1: $R_1$ is (E)-3-(4-isoquinolinyl)-2-propenyl, $R_2$ is H, $R_3$ is H, $R_7$ is H. $R_8$ is Ethyl)

A solution of the product of Reference Example 18 (75 mg, 0.100 mmol), triethylsilane (0.064 mL, 0.40 mmol), trifluoroacetic acid (0.031 mL, 0.40 mmol), and (E)-3-(4-isoquinolinyl)-2-propenal (product of Reference Example 44; 92 mg, 0.503 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 13.4 mg (17%) of the title compound as a colorless solid. MS 808 $(M+H)^+$.

EXAMPLE 28

Compound 31 (Formula 1: $R_1$ is (E)-3-(7-quinolinyl)-2-propenyl, $R_2$ is H, $R_3$ is H, $R_7$ is H, $R_8$ is Ethyl)

A solution of the product of Reference Example 18 (75 mg, 0.10 mmol), triethylsilane (0.064 mL, 0.40 mmol), trifluoroacetic acid (0.031 mL, 0.40 mmol), and (E)-3-(7-quinolinyl)-2-propenal (product of Reference Example 38; 92 mg, 0.50 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 14 mg (17%) of the title compound as a colorless solid. MS 808 $(M+H)^+$.

EXAMPLE 29

Compound 32 (Formula 1: $R_1$ is (E)-3-[(2-fluoro-4-pyrimidin-2-yl)phenyl]-2-propenyl, $R_2$ is H, $R_3$ is H, $R_7$ is H, $R_8$ is Ethyl)

A solution of the product of Reference Example 18 (65 mg, 0.087 mmol), triethylsilane (0.014 mL, 0.35 mmol), trifluoroacetic acid (0.026 mL, 0.35 mmol), and (E)-3-[(2-fluoro-4-pyrimidin-2-yl)phenyl]-2-propenal (product of Reference Example 45; 99 mg, 0.436 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 10.2 mg (14%) of the title compound as a colorless solid. MS 853 $(M+H)^+$.

EXAMPLE 30

Compound 33 (Formula 1: $R_1$ is (E)-3-(2-pyridinyl)-2-propenyl, $R_2$ is H, $R_3$ is H, $R_7$ is H, $R_8$ is Ethyl)

A solution of the product of Reference Example 18 (55 mg, 0.074 mmol), triethylsilane (0.047 mL, 0.295 mmol), trifluoroacetic acid (0.023 mL, 0.295 mmol), and (E)-3-(2-pyridinyl)-2-propenal (prepared as described in *J. Med. Chem.* 1975, 18,839; 49 mg, 0.37 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 3.8 mg (7%) of the title compound as a colorless solid. MS 759 $(M+H)^+$.

EXAMPLE 31

Compound 34 (Formula 1: $R_1$ is (E)-3-(3-pyridinyl)-2-propenyl, $R_2$ is H, $R_3$ is H, $R_7$ is H, $R_8$ is Ethyl)

A solution of the product of Reference Example 18 (75 mg, 0.1 mmol), triethylsilane (0.064 mL, 0.40 mmol), trifluoroacetic acid (0.031 mL, 0.40 mmol), and (E)-3-(3-pyridinyl)-2-propenal (prepared as described in *Angew. Chem.* 1975, 87, 486; 67 mg, 0.50 mmol) in $CH_3CN$ (0.5 mL) was stirred at 25° C. for 20 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 29.2 mg (38%) of the title compound as a colorless foam. MS 759 $(M+H)^+$.

EXAMPLE 32

Compound 35 (Formula 1: $R_1$ is (E)-3-(2-phenylpyridin-5-yl)-2-propenyl, $R_2$ is H, $R_3$ is H, $R_7$ is H, $R_8$ is Ethyl)

A solution of the product of Reference Example 18 (70 mg, 0.094 mmol), triethylsilane (0.06 mL, 0.370 mmol), trifluoroacetic acid (0.029 mL, 0.376 mmol), and (E)-3-(2-phenylpyridin-5-yl)-2-propenal (product of Reference Example 34; 98 mg, 0.409 mmol) in $CH_3CN$ (0.5 mL) was stirred at 25° C. for 48 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 14.2 mg (18%) of the title compound as a colorless solid. MS 835 $(M+H)^+$.

EXAMPLE 33

Compound 36 (Formula 1: $R_1$ is (E)-4-[2-(2-quinolinyl)ethenyl]benzyl, $R_2$ is H, $R_3$ is H, $R_7$ is H, $R_8$ is Ethyl)

A solution of the product of Reference Example 18 (75 mg, 0.100 mmol), triethylsilane (0.080 mL, 0.503 mmol), trifluoroacetic acid (0.080 mL, 0.503 mmol), and (E)-4-[2-(2-quinolinyl)ethenyl]benzaldehyde (prepared as described in *J. Med. Chem.* 1997, 40,1075; 130 mg, 0.503 mmol) in $CH_3CN$ (0.5 mL) was stirred at 25° C. for 30 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 20 mg (23%) of the title compound as a colorless foam. MS 885 $(M+H)^+$.

EXAMPLE 34

Compound 37 (Formula 1: $R_1$ is (E)-3-[1-(2-pyrimidinyl)-1H-imidazol-4-yl]-2-propenyl, $R_2$ is H, $R_3$ is H, $R_7$ is H, $R_8$ is Ethyl)

A solution of the product of Reference Example 18 (75 mg, 0.100 mmol), triethylsilane (0.080 mL, 0.503 mmol), trifluoroacetic acid (0.038 mL, 0.503 mmol), and (E)-3-[1-(2-pyrimidinyl)-1H-imidazol-4-yl]-2-propenal (product of Reference Example 40; 101 mg, 0.503 mmol) in $CH_3CN$ (0.5 mL) was stirred at 25° C. for 36 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 17.2 mg (21%) of the title compound as a colorless foam. MS 825 $(M+H)^+$.

EXAMPLE 35

Compound 38 (Formula 1: $R_1$ (E)-3-(6-quinoxalinyl)-2-propenyl, $R_2$ is H, $R_3$ is H, $R_7$ is H, $R_8$ is ethyl) A solution of the product of Reference Example 18 (75 mg, 0.100 mmol), triethylsilane (0.064 mL, 0.403 mmol), trifluoroacetic acid (0.031 mL, 0.403 mmol), and (E)-3-(6-quinoxalinyl)-2-propenal (product of Reference Example 28; 92 mg, 0.503 mmol) in $CH_3CN$ (0.2 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 13.4 mg (17%) of the title compound as a colorless foam. MS 808 $(M+H)^+$.

EXAMPLE 36

Compound 39 (Formula 1: $R_1$ is (E)-3-(4-quinolinyl)-2-propenyl, $R_2$ is H, $R_3$ is H, $R_7$ is H, $R_8$ is Ethyl)

A solution of the product of Reference Example 18 (100 mg, 0.13 mmol), triethylsilane (0.120 mL, 0.800 mmol), trifluoroacetic acid (0.07 mL, 0.800 mmol), and (E)-3-(4-quinolinyl)-2-propenal (prepared as described in EP676409; 119 mg, 0.65 mmol) in $CH_3CN$ (0.5 mL) was stirred at 25° C. for 18 h. The reaction mixture was diluted with ethyl acetate (20 mL), washed with sat. aq. $NaHCO_3$ (20 mL) and brine (20 mL), dried ($Na_2SO_4$), and concentrated. The residue was dissolved in methanol (2 mL) and was warmed to reflux for 12 h. Purification by chromatography ($SiO_2$, 94:6:0.5 dichloromethane/methanol/conc. $NH_4OH$) yielded 1.7 mg (1.6%) of the title compound as a colorless foam. MS 808 (M+H).

EXAMPLE 37

Compound 40 (Formula 1: $R_1$ is (E)-3-(3-pyrimidinylpyridin-5-yl)-2-propenyl, $R_2$ is H, $R_3$ is H, $R_7$ is H, $R_8$ is Ethyl)

The product of Reference Example 18 (71 mg, 0.10 mmol) and 3-bromo-5-(2-pyrimidinyl)pyridine (product of Reference Example 43; 47 mg, 0.20 mmol) were mixed in degassed acetonitrile (2 mL). After 5 min, the reaction mixture was treated with tri-ortho-tolylphosphine (6.1 mg, 0.02 mmol), triethylamine (0.03 mL, 0.22 mmol) and palladium acetate (2.3 mg, 0.01 mmol). The resulting mixture was warmed to reflux. After 14 h, the reaction mixture was allowed to cool to room temperature, diluted with ethyl acetate (25 mL), washed with satd. aqueous $KH_2PO_4$ (25 mL), the organic layer separated, and dried ($MgSO_4$). The reaction mixture organic layer was filtered and concentrated in vacuo. The residue was diluted with methanol (2 mL) and allowed to stir for 12 h. The reaction mixture was concentrated in vacuo and purification purified by flash chromatography (0–5% MeOH/EtOAc containing 0.5% $NH_4OH$) afforded 1.3 mg (1.5%) as white foam. MS 836 $(M+H)^+$.

REFERENCE EXAMPLE 1

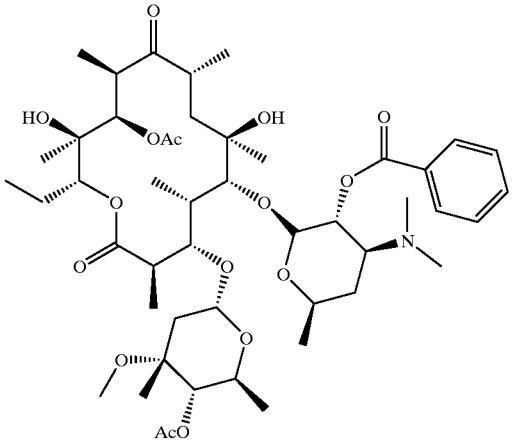

A suspension of erythromycin A (5.0 g, 6.81 mmol) in $CH_2Cl_2$ (25 mL) at 25° C. was treated with benzoic anhydride (1.69 g, 7.49 mmol, 1.1 equivalents) and triethylamine (1.43 mL, 7.49 mmol, 1.1 equivalents) and the reaction mixture was allowed to stir. After 18 h, additional benzoic anhydride (0.3 g, 1.33 mmol, 0.2 equivalents) and triethylamine (0.25 mL, 1.33 mmol, 0.2 equivalents) was added and the reaction mixture was allowed to stir an additional 18 h. The reaction mixture was diluted with ethyl acetate (100 mL), washed with satd. aqueous $NaHCO_3$ (2×100 mL), brine (1×100 mL), dried ($MgSO_4$), filtered, and concentrated in vacuo. The residue was dissolved in pyridine (35 mL), treated with acetic anhydride (1.93 mL, 20.4 mmol, 3 equivalents), triethylamine (2.85 mL, 14.9 mmol, 2.2 equivalents) and DMAP (0.166 g, 1.36 mmol, 0.2 equivalents). The resulting solution was allowed to stir for 18 h, diluted with ethyl acetate (100 mL), washed with satd. aqueous NaHCO$_3$ (2×100 mL), brine (1×100 mL), dried (MgSO$_4$), filtered, and concentrated in vacuo to afford the title compound (6.27 g, 100%) as an off-white foam. This residue was used without any further purification. MS 923 (M+H)$^+$.

REFERENCE EXAMPLE 2

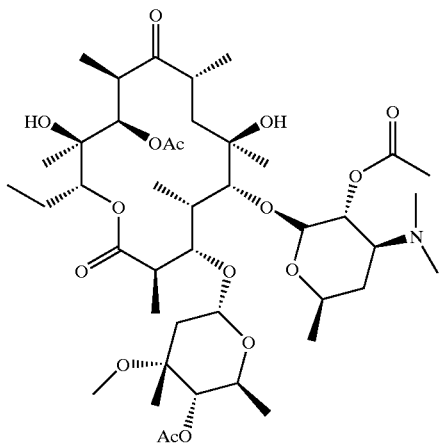

A solution of erythromycin A (20.0 g, 27.2 mmol) in pyridine (100 mL) was treated with acetic anhydride (12.9 mL, 136 mmol, 5 equivalents), triethylamine (19 mL, 136 mmol, 5 equivalents) and DMAP (0.166 g, 1.36 mmol, 0.2 equivalents). The resulting solution was allowed to stir for 18 h, diluted with ethyl acetate (400 mL), washed with satd. aqueous NaHCO$_3$ (2×200 mL), brine (1×200 mL), dried (MgSO$_4$), filtered, and concentrated in vacuo to afford the title compound (24.2 g, 104%) as an off-white foam. This residue was used without any further purification. MS 861 (M+H)$^+$.

REFERENCE EXAMPLE 3

Alternate Preparation of the Product of Reference Example 2

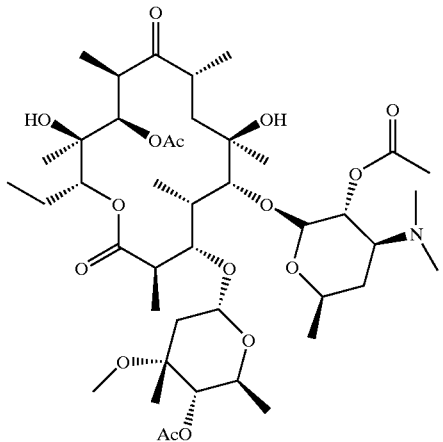

Triethylamine (42.0 mL, 301 mmol), DMAP (0.6 g, 4.9 mmol), and acetic anhydride (28.5 mL, 302 mmol) were added to a 0° C. suspension of erythromycin (36.7 g, 50 mmol) in dichloromethane (250 mL). The mixture was allowed to warm to room temperature and stir for 18 h. Methanol (10 mL) was added and stirring was continued for 5 min. The mixture was diluted with ether (750 mL), washed with sat. aq. NaHCO$_3$, water, and brine (500 mL each), dried (MgSO$_4$), and concentrated to provide the title compound as a colorless foam. The material was used in the next step without further purification. MS 861 (M+H)$^+$.

REFERENCE EXAMPLE 4

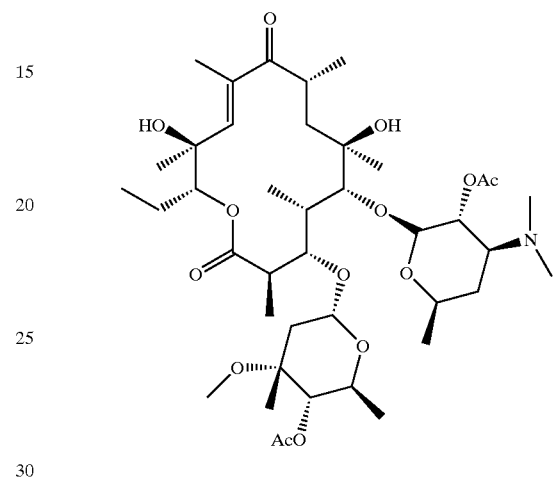

Sodium hexamethyldisilazide (1.0M in THF, 60.0 mL, 60.00 mmol) was added over 25 min to a 0° C. solution of the product from Reference Example 3 (50.0 mmol) in THF (500 mL). After 2 h at 0° C., the mixture was diluted with water (250 mL) and brine (250 mL) and extracted with ethyl acetate (3×250 mL). The combined organic layers were dried (MgSO$_4$) and concentrated. The material was used in the next step without further purification. If desired, pure material could be obtained by chromatography (SiO$_2$, 95:5:0.2 dichloromethane/methanol/conc. NH$_4$OH). MS 800 (M+H)$^+$.

REFERENCE EXAMPLE 5

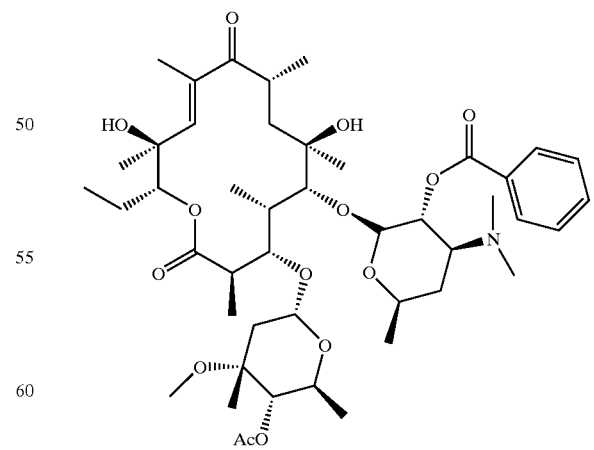

A solution of the product of Reference Example 1 (6.33 g, 6.86 mmol) in THF (60 mL) at 0° C. was treated with a solution of NaHMDS (8.23 mL, 8,23 mmol, 1.2 equivalents)

via a dropping funnel over 30 minutes. The reaction mixture was allowed to stir for 2 h at 0° C. The reaction mixture was quenched with brine (10 mL), allowed to warm to 25° C., diluted with ethyl acetate (150 mL), washed with brine (2×75 mL), dried (MgSO$_4$), filtered, and concentrated in vacuo to afford the title compound (5.93 g, 100%) an off-white foam which was used without further purification. MS 963 (M+H)$^+$

REFERENCE EXAMPLE 6

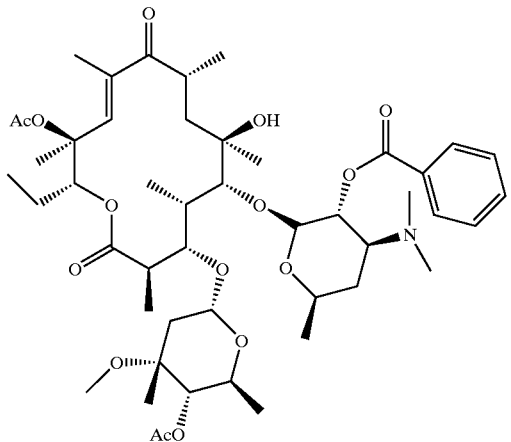

The product of Reference Example 5 was dissolved in pyridine (35 mL) and treated with acetic anhydride (1.62 mL), triethylamine (2.39 mL) and dimethylaminopyridine (0.166 g) and the reaction mixture was allowed to stir. After 18 h, the reaction mixture was diluted with ethyl acetate (100 mL), washed with saturated aqueous NaHCO$_3$ (2×100 mL), washed with brine (1×100 mL), and dried over (MgSO$_4$). The solution was filtered and concentrated in vacuo to afford an off-white foam. Purification by flash chromatography (1% hexanes/EtOAc) afforded the title compound (3.92 g, 66%) as an off-white solid. MS 905 (M+H)$^+$.

REFERENCE EXAMPLE 7

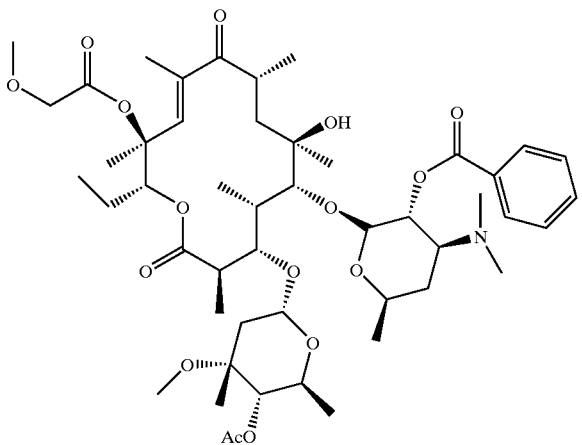

A solution of methoxy acetic acid (1.25 mL, 15.6 mmol) and DMAP (61 mg, 0.5 mmol) in Et2O (5 mL) was treated with DCC (Dicyclohexylcarbodiimide, 3.2 g, 15.6 mmol) at 25° C. After 15 min, a solution of the product from Reference Example 5 (5 g, 6.25 mmol) in pyridine (15 mL) was added and the resulting mixture was allowed to stir for 12 h. The reaction mixture was quenched by the addition of water (20 mL) and stirred for an additional 20 min. The mixture was diluted with EtOAc (100 mL), and the organic layer was washed with 10% aqueous NAOH (2×100 mL), dried (MgSO$_4$), filtered and concentrated in vacuo. Purification by flash chromatography (1% hexanes/EtOAc) afforded the title compound (3.92 g, 67%) as an off-white solid. MS 935 (M+H)$^+$.

REFERENCE EXAMPLE 8

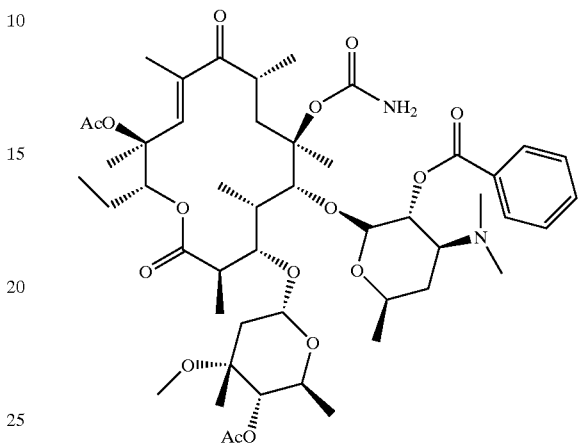

A solution of the product of Reference Example 6 (3.90 g, 4.31 mmol) in CH$_2$Cl$_2$ (30 mL) at 0° C. was treated with a trichloroacetylisocyanate (1.04 mL, 9.04 mmol, 2.1 equivalents) via syringe over 5 minutes. The reaction mixture was stirred for 20 min at 0° C., allowed to warm to 25° C., and concentrated in vacuoto afford a light brown foam. This residue was dissolved in ethyl acetate (35 mL), treated with 10% aqueous sodium hydroxide (20 mL), and stirred for 1 h. The mixture was diluted with ethyl acetate (100 mL), and the organic layer was washed with saturated aqueous NaHCO$_3$ (2×100 mL), washed with brine (1×100 mL), and dried over Na$_2$SO$_4$. The solution was filtered and concentrated in vacuo to afford an off-white foam. Purification by flash chromatography (2% MeOH/EtOAc) afforded the title compound (3.07 g, 75%) as an off-white solid. MS 948 (M+H)$^+$.

REFERENCE EXAMPLE 9

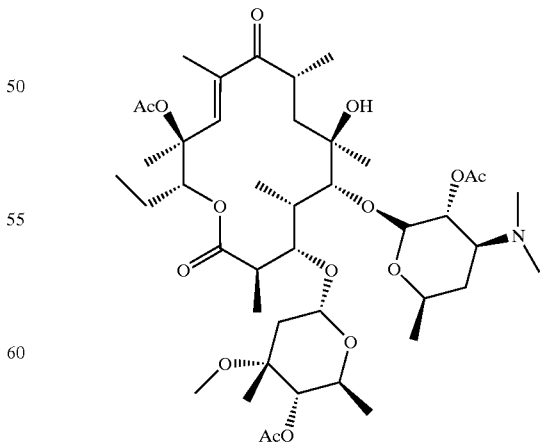

The product of Reference Example 4 (6.0 g, 7.50 mmol) was dissolved in pyridine (50 mL) and treated with acetic anhydride (1.77 mL), triethylamine (2.61 mL) and dimethylaminopyridine (0.092 g) and the reaction mixture was allowed to stir. After 18 h, the reaction mixture was diluted with ethyl acetate (100 mL), washed with saturated aqueous NaHCO₃ (2×100 mL), washed with brine (1×100 mL), and dried over (MgSO₄). The solution was filtered and concentrated in vacuo to afford an off-white foam. Purification by flash chromatography (1% hexanes/EtOAc) afforded the title compound (3.92 g, 60%) as an off-white solid. MS 843 (M+H)⁺.

REFERENCE EXAMPLE 10

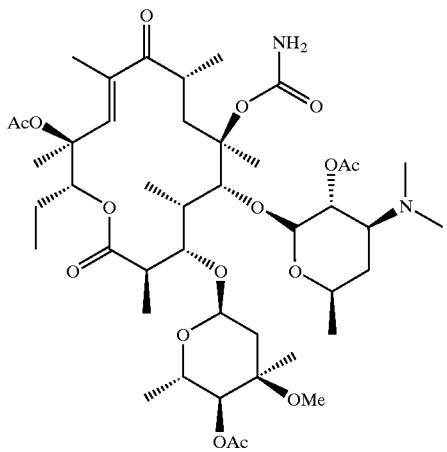

A solution of the product of Reference Example 9 (2.00 g, 2.37 mmol) in CH₂Cl₂ (30 mL) at 0° C. was treated with a trichloroacetylisocyanate (0.54 mL, 4.75 mmol, 2.1 equivalents) via syringe over 5 minutes. The reaction mixture was stirred for 20 min at 0° C., allowed to warm to 25° C., and concentrated in vacuoto afford a light brown foam. This residue was dissolved in ethyl acetate (35 mL), treated with 10% aqueous sodium hydroxide (20 mL), and stirred for 1 h. The mixture was diluted with ethyl acetate (100 mL), and the organic layer was washed with saturated aqueous NaHCO₃ (2×100 mL), washed with brine (1×100 mL), and dried over Na₂SO₄. The solution was filtered and concentrated in vacuo to afford an off-white foam. Purification by flash chromatography (2% MeOH/EtOAc) afforded the title compound (1.37 g, 65%) as an off-white solid. MS 886 (M+H)⁺.

REFERENCE EXAMPLE 11

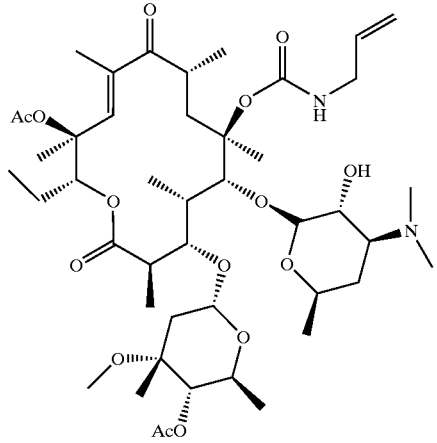

A solution of the product of Reference Example 10 (1.81 g, 2.04 mmol) in MeOH (25 mL) at 0° C. was sequentially treated with allyl phenyl selenide (1.3 mL, 8.6 mmol), Et₃N (2.23 mL, 16 mmol), and NCS (1.08 g, 8.1 mmol). After 5 min the reaction mixture was allowed to warm to 25° C. and was stirred for 16 h. The reaction mixture was diluted with EtOAc (100 mL), and the organic layer was washed with 0.5 M aqueous KH₂PO₄ (2×50 mL), washed with brine (1×50 mL), and dried over MgSO₄. The solution was filtered and concentrated in vacuo. Purification of the residue by flash chromatography (0–5% MeOH/EtOAc containing 0.5% conc. NH₄OH) afforded the title compound (0.757 g, 42%) as a white foam. MS 884 (M+H)⁺.

REFERENCE EXAMPLE 12

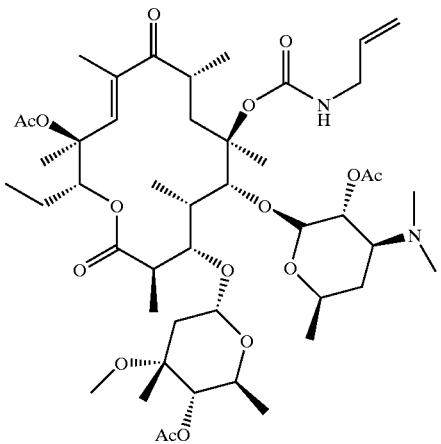

A solution of the product of Reference Example 11 (1.31 g, 1.48 mmol) in CH₂Cl₂ (30 mL) at 25° C. is treated with acetic anhydride (0.35 mL, 3.70 mmol, 2.5 equivalents), and triethylamine (0.52 mL, 3.70 mmol, 2.5 equivalents). The resulting solution was allowed to stir for 18 h, diluted with ethyl acetate (100 mL), washed with satd. aqueous NaHCO₃ (2×50 mL), brine (1×50 mL), dried (MgSO₄), filtered, and concentrated in vacuo to afford the title compound (1.21 g, 104%) as an off-white foam. This residue was used without any further purification. MS 926 (M+H)⁺.

REFERENCE EXAMPLE 13

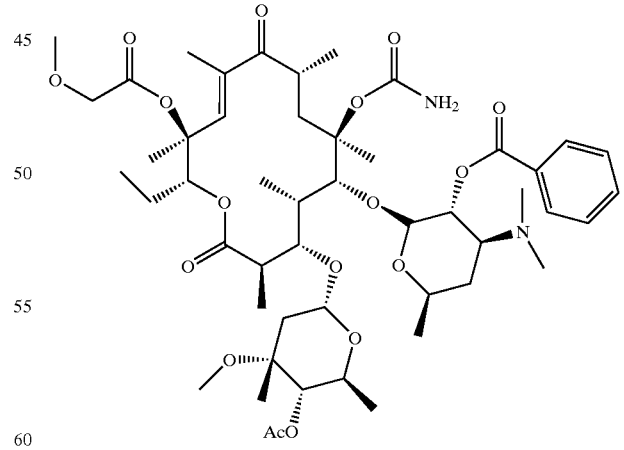

A solution of the product of Reference Example 7 (2.5 g, 2.671 mmol) in CH₂Cl₂ (15 mL) at 0° C. was treated with a trichloroacetylisocyanate (0.77 mL, 6.69 mmol, 2.5 equivalents) via syringe over 5 minutes. The reaction mixture was stirred for 20 min at 0° C., allowed to warm to 25° C., and concentrated in vacuo to afford a light brown foam.

This residue was dissolved in ethyl acetate (35 mL), treated with 10% aqueous sodium hydroxide (20 mL), and the mixture was stirred for 1 h. The reaction mixture was diluted with ethyl acetate (100 mL), washed with saturated aqueous NaHCO₃ (2×100 mL), washed with brine (1×100 mL), and dried over Na₂SO₄. The solution was filtered and concentrated in vacuo to afford an off-white foam. Purification by flash chromatography (2% MeOH/EtOAc) afforded the title compound (1.42 g, 54%) as an off-white solid. MS 978 (M+H)⁺.

REFERENCE EXAMPLE 14

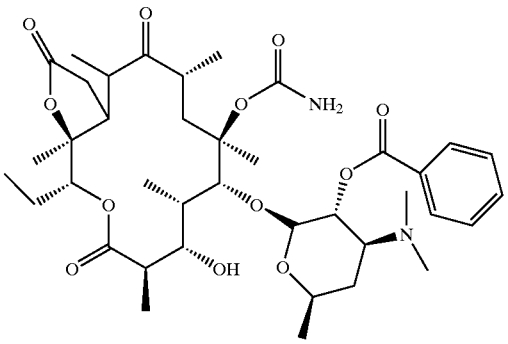

To a solution of diisopropylamine (2.66 mL, 19.0 mmol, 6 equivalents) in THF (33 mL) at 0° C. was carefully added n-butyllithium (7.60 mL, 19.0 mmol, 2.5 M in hexanes, 6 equivalents) via a syringe over 5 minutes. The resulting solution was allowed to stir for 20 min at 0° C., was cooled to −78° C., and was treated with a solution of the product of Reference Example 8 (3.00 g, 3.16 mmol) in THF (25 mL) over 20 min (the reaction mixture thickened once approximately half the solution was added). The resulting slurry was allowed to warm to −10° C. (ice/acetone) and stirred for 2 h (the reaction mixture became thinner, but not homogenous). The reaction mixture was quenched with saturated aqueous NH₄Cl (50 mL), and warmed to 25° C. The resulting solution was diluted with ethyl acetate (100 mL), and the organic layer was washed with saturated aqueous NH₄Cl (2×50 mL), and concentrated in vacuo. The residue was diluted with methanol (40 mL) and was treated with 10% aqueous HCl. After 36 h, the pH of the reaction mixture was adjusted to ~8 with concentrated NH₄OH. The resulting solution was washed with ethyl acetate (3×100 mL), the organic layers were combined, dried (MgSO₄), filtered, and concentrated in vacuo to afford a brown oil. Purification by flash chromatography (0–5% MeOH/EtOAc) afforded the title compound (1.04 g, 44%) as a brownish foam. MS 747 (M+H)⁺.

REFERENCE EXAMPLE 15

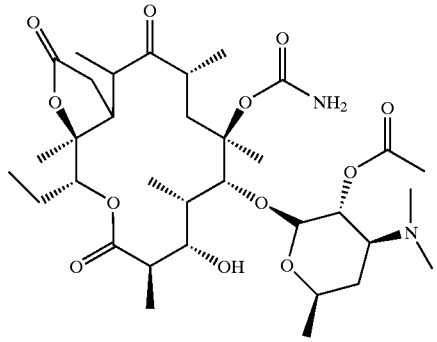

The title compound was prepared by a procedure analogous to Reference Example 14, except that the product of Reference Example 10 was used in place of the product of Reference Example 8. MS 685 (M+H)⁺.

REFERENCE EXAMPLE 16

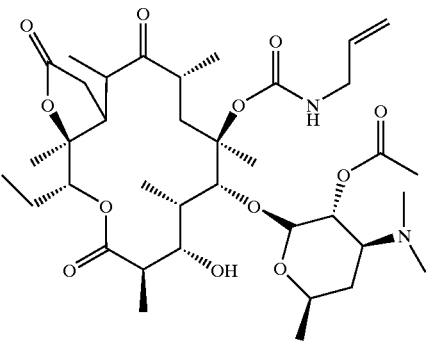

The title compound was prepared by a procedure analogous to Reference Example 14, except that the product of Reference Example 12 was used in place of the product of Reference Example 8. MS 725 (M+H)⁺.

REFERENCE EXAMPLE 17

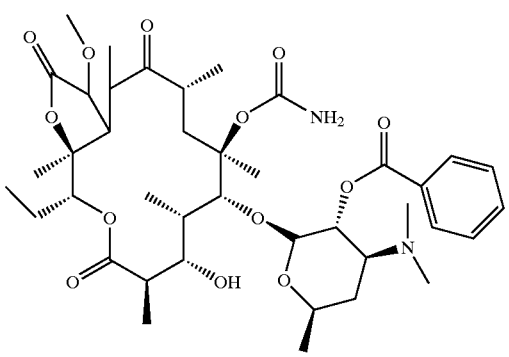

To a solution of diisopropylamine (1.22 mL, 8.71 mmol, 6 equivalents) in THF (15 mL) at 0° C. was carefully added n-butyllithium (3.5 mL, 8.7 mmol, 2.5 M in hexanes, 6 equivalents) via syringe over 5 minutes. The resulting solution was stirred for 20 min at 0° C., was cooled to −78° C., and was treated with a solution of the product of Reference Example 13 (1.42 g, 1.45 mmol) in THF over 20 min (the reaction mixture thickened once approximately half of the solution was added). The resulting slurry was allowed to warm to −10° C. (ice/acetone) and stirred for 2 h (the reaction mixture became thinner, but not homogenous). The reaction mixture was quenched with saturated aqueous NH₄Cl (50 mL), and allowed to warm to 25° C. The resulting solution was diluted with ethyl acetate (100 mL), and the organic layer was washed with saturated aqueous NH₄Cl (2×50 mL), and concentrated in vacuo. The residue was diluted with methanol (40 mL) and was treated with 10% aqueous HCl. After 12 h, the pH of the reaction mixture was adjusted to ~8 with concentrated NH₄OH. The resulting solution was washed with ethyl acetate (3×100 mL), the organic layers were combined, and dried over MgSO₄. The solution was filtered, and concentrated in vacuo to afford a brown oil. Purification by flash chromatography (0–5% MeOH/CH₂Cl₂ containing 0.5% NH₄OH) afforded the title compound (0.800 g, 71%) as a brownish foam. MS 777 (M+H)⁺.

REFERENCE EXAMPLE 18

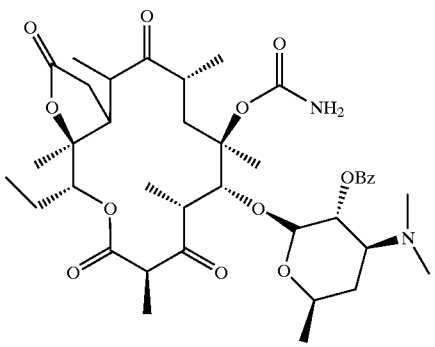

A solution of the product of Reference Example 14 (1.00 g, 1.33 mmol) in CH$_2$Cl$_2$ (10 mL) at 0° C. was treated with EDCI (1.03 g, 5.35 mmol, 4.0 equivalents) and DMSO (0.73 mL, 9.37 mmol, 7.0 equivalents). After 5 min, the resulting suspension was treated with a solution of pyridinium trifluoroacetate (1.03 g, 5.35 mmol, 4.0 equivalents) in CH$_2$Cl$_2$ (10 mL) over 30 min via dropping funnel. The resulting homogeneous solution was allowed to warm to 25° C., stirred for 2 h, diluted with water (2 mL) and stirred an additional 15 min. The reaction mixture was diluted with CH$_2$Cl$_2$ (30 mL), washed with brine (2×25 mL), dried (MgSO$_4$), filtered, and concentrated in vacuo. Purification by flash chromatography (EtOAc) afforded the title compound (0.521 g, 53%) as a white solid. MS 745 (M+H)$^+$.

REFERENCE EXAMPLE 19

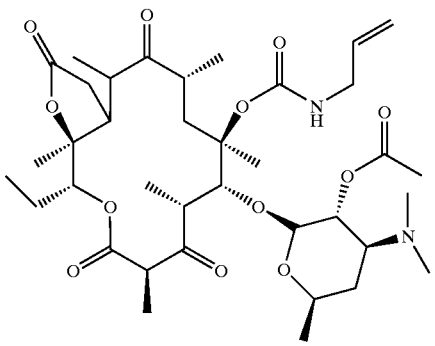

The title compound was prepared by a procedure analogous to Reference Example 18 except that the product of Reference Example 16 was used in place of the product of Reference Example 14. MS 723 (M+H)$^+$.

REFERENCE EXAMPLE 20

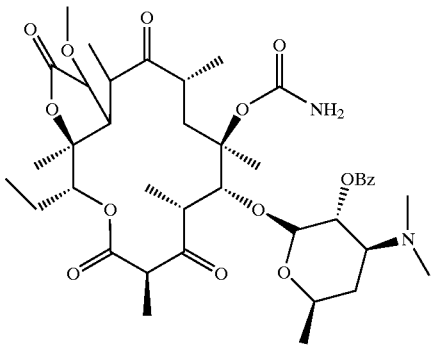

A solution of the product of Reference Example 17 (0.80 g, 1.03 mmol) in CH$_2$Cl$_2$ (10 mL) at 0° C. was treated with EDCI (0.96 g, 5.35 mmol, 5.0 equivalents) and DMSO (0.71 mL, 10.4 mmol, 10 equivalents). After 5 min, the resulting suspension was treated with a solution of pyridinium trifluoroacetate (0.99 g, 5.17 mmol, 5.0 equivalents) in CH$_2$Cl$_2$ (10 mL) over 30 min via dropping funnel. The resulting homogeneous solution was allowed to warm to 25° C., stirred for 2 h, diluted with water (2 mL) and stirred an additional 15 min. The reaction mixture was diluted with CH$_2$Cl$_2$ (30 mL), washed with brine (2×25 mL), dried (MgSO$_4$), filtered, and concentrated in vacuo. Purification by flash chromatography (EtOAc) afforded the title compound (0.35 g, 44%) as a light brown solid. MS 775 (M+H)$^+$.

REFERENCE EXAMPLE 21

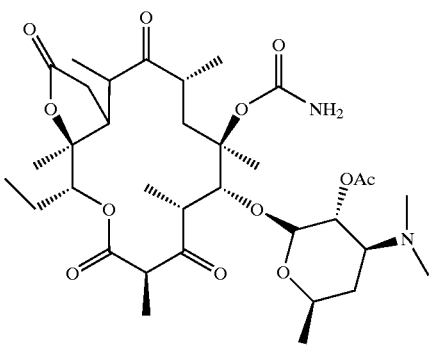

The title compound was prepared by a procedure analogous to Reference Example 20 except that the product of Reference Example 15 was used in place of the product of Reference Example 17. MS 683 (M+H)$^+$.

REFERENCE EXAMPLE 22

1-(2-Pyrimidinyl)-1H-imidazole-4-carboxaldehyde

Sodium hydride (60% in oil, 1.44 g, 36.00 mmol) was added to a 0° C. solution of 1H-imidazole-4-carboxaldehyde (4.40 g, 36.03 mmol) in DMF (16 mL). After stirring for 20 min at 0° C., the mixture was allowed to warm to RT and a solution of 2-chloropyrimidine (4.12 g, 35.97 mmol) in DMF (8 mL) was added. The resulting mixture was heated to 100° C. for 18 h. The solvent was evaporated, the residue was dissolved in ethyl acetate, washed with water and brine, dried (MgSO$_4$), and concentrated to provide 6.20 g (86%) of the title compound. MS 175 (M+H)$^+$.

REFERENCE EXAMPLE 23

3-(2-Pyridinyl)benzaldehyde 2M aq. Na$_2$CO$_3$ (5 mL) and a solution of 3-formylphenylboronic acid (1.14 g, 7.60 mmol) in methanol (5 mL) were added to a solution of 2-bromopyridine (1.00 g, 6.33 mmol) and tetrakis(triphenylphosphine)palladium(0) (0.22 g, 0.19 mmol) in toluene (10 mL) and the mixture was heated to reflux for 18 h. The cooled reaction mixture was diluted with dichloromethane, washed with sat. aq. NaHCO$_3$ and brine, dried (MgSO$_4$), and concentrated. Purification by chromatography (SiO$_2$, 4:1 hexane/ethyl acetate) yielded 1.03 g (89%) of the title compound. MS 184(M+H)$^+$.

REFERENCE EXAMPLE 24

3-(2-Pyrimidinyl)benzaldehyde

A mixture of $Na_2CO_3$ (4.74 g, 44.72 mmol) and 3-formylphenylboronic acid (3.40 g, 22.67 mmol) in water (15 mL) were added to a solution of 2-bromopyrimidine (3.00 g, 18.87 mmol) and tetrakis(triphenylphosphine)palladium(0) (0.72 g, 0.62 mmol) in DME (30 mL) and the mixture was heated to reflux for 24 h. The cooled reaction mixture was diluted with dichloromethane, washed with sat. aq. $NaHCO_3$ and brine, dried ($MgSO_4$), and concentrated. Purification by chromatography ($SiO_2$, 1:1 hexane/ethyl acetate) yielded 2.20 g (63%) of the title compound. MS 185 $(M+H)^+$.

REFERENCE EXAMPLE 25

4-(5-Pyrimidinyl)benzaldehyde

1 M aq. $Na_2CO_3$ (20 mL) and ethanol (10 mL) were added to a solution of 5-chloropyrimidine hydrochloride (3.03 g, 20.06 mmol, prepared as described in WO 9821188), 4-formylphenylboronic acid (3.90 g, 26.01 mmol) and [1,4-bis(diphenylphosphino)butane]palladium(II) dichloride (0.60 g, 0.99 mmol) in toluene (40 mL) and the mixture was heated to reflux for 18 h. The cooled reaction mixture was diluted with ethyl acetate, washed with sat. aq. $NaHCO_3$ and brine, dried ($MgSO_4$), and concentrated. Purification by chromatography ($SiO_2$, 4:1 hexane/ethyl acetate) yielded 1.80 g (42%) of the title compound. MS 185 $(M+H)^+$.

REFERENCE EXAMPLE 26

2-Fluoro-4-(2-pyrimidinyl)benzaldehyde

Step A:

Dimethyl sulfoxide (70 mL) and 4-bromo-2-fluorobenzaldehyde (2.44 g, 12.02 mmol) were added to a mixture of potassium acetate (3.54 g, 36.07 mmol), bis(pinacolato)diboron (3.36 g, 13.23 mmol), and [1,1'-bis(diphenylphosphino)ferrocene]dichloropalladium(II) (294 mg, 0.36 mmol). The mixture was heated to 80° C. for 18 h. The cooled reaction mixture was diluted with benzene, washed with water, dried ($MgSO_4$), and concentrated. The material was used in the next step without further purification.

Step B:

The title compound was prepared by a procedure analogous to Reference Example 24 by substituting the product of step A for the 3-formylphenylboronic acid of Reference Example 24. MS 203 $(M+H)^+$.

REFERENCE EXAMPLE 27

(E)-3-[4-(3-Pyridinyl)phenyl]-2-propenal 2M aq. $Na_2CO_3$ (1 mL) and a solution of 3-pyridinylboronic acid (148 mg, 1.20 mmol) in methanol (1 mL) were added to a solution of 4-bromocinnamaldehyde (211 mg, 1.00 mmol, prepared as described in *Tetrahedron* 1998, 54, 10761) and tetrakis(triphenylphosphine)palladium(0) (35 mg, 0.030 mmol) in toluene (2 mL) and the mixture was heated to reflux for 36 h. The cooled reaction mixture was diluted with dichloromethane, washed with sat. aq. $NaHCO_3$ and brine, dried ($MgSO_4$), and concentrated. Purification by chromatography ($SiO_2$, 1:1 hexane/ethyl acetate) yielded the title compound. MS 210 $(M+H)^+$.

REFERENCE EXAMPLE 28

(E)-3-(6-Quinoxalinyl)-2-propenal

A mixture of 6-quinoxalinecarboxaldehyde (0.62 g, 3.92 mmol, prepared as described in *Photochem. Photobiol.* 1991, 54, 7), (1,3-dioxolan-2-ylmethyl)triphenylphosphonium bromide (2.50 g, 5.82 mmol), and TDA-1 (1.20 mL, 3.75 mmol) in dichloromethane (20 mL) and sat. aq. $K_2CO_3$ (20 mL) was heated to reflux for 4 h. The layers were separated and the aqueous layer was extracted with dichloromethane (2×20 mL). The combined organic layers were washed with water (50 mL) and brine (50 mL), dried ($Na_2SO_4$), and concentrated. THF (10 mL) and 10% HCl (10 mL) were added and the mixture was stirred for 1 h at rt. The mixture was cooled to 0° C., the precipitated solids were removed by filtration, washed with water and dried in vacuo to give 0.47 g (65%) of the title compound as a tan solid. MS 185 $(M+H)^+$.

REFERENCE EXAMPLE 29

(E)-3-(6-Quinolinyl)-2-propenal

A mixture of 6-quinolinecarboxaldehyde (1.58 g, 10.05 mmol, prepared as described in U.S. Pat. No. 5,559,256), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. $K_2CO_3$ (50 mL) was heated to reflux for 5 h. The layers were separated and the aqueous layer was extracted with dichloromethane (2×25 mL). The combined organic layers were washed with water (50 mL) and brine (50 mL), dried ($MgSO_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried ($MgSO_4$), and concentrated. Chromatography ($SiO_2$, 1:1 hexane/ethyl acetate+0.2% triethylamine) provided a yellow solid that was partitioned between ethyl acetate (20 mL) and 10% HCl (15 mL). The aqueous layer was washed with ethyl acetate (2×20 mL) and then made basic with 10% NaOH. The precipitated solids were collected by filtration, washed with water, and dried in vacuo to give 1.20 g (65%) of the title compound as a light yellow solid. MS 184 $(M+H)^+$.

REFERENCE EXAMPLE 30

(E)-3-[4-(2-Pyrimidinyl)phenyl]-2-propenal

A mixture of 4-(2-pyrimidinyl)-benzaldehyde (1.83 g, 9.94 mmol, prepared as described in WO 9828264), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. $K_2CO_3$ (50 mL) was heated to reflux for 20 h. The layers were separated and the aqueous layer was extracted with dichloromethane (2×25 mL). The combined organic layers were washed with water (50 mL) and brine (50 mL), dried ($MgSO_4$), and concentrated. THF (25 mL) and 10% HCl (25 mL) were added and the mixture was stirred for 1 h at rt. The mixture was cooled to 0° C., the precipitated solids were removed by filtration, washed with water and air-dried. Recrystallization from 2-propanol provided 1.20 g (57%) of the title compound as a light yellow solid. MS 211 $(M+H)^+$.

REFERENCE EXAMPLE 31

(E)-3-[4-(2-Pyridinyl)phenyl]-2-propenal

A mixture of 4-(2-pyridinyl)-benzaldehyde (1.76 g, 9.58 mmol), (1,3-dioxolan-2-ylmethyl)triphenylphosphonium bromide (6.45 g, 15.02 mmol), and TDA-1 (Tris(3,6- dioxaheptyl)amine, 3.20 mL, 10.00 mmol) in dichloromethane (50 mL) and sat. aq. K₂CO₃ (50 mL) was heated to reflux for 20 h. The layers were separated and the aqueous layer was extracted with dichloromethane (2×25 mL). The combined organic layers were washed with water (50 mL) and brine (50 mL), dried (MgSO₄), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried (MgSO₄), and concentrated. Purification by chromatography (SiO₂, 3:1 hexane/ethyl acetate) provided 1.69 g (89%) of the title compound as a yellow solid. MS 210 (M+H)⁺.

REFERENCE EXAMPLE 32

(E)-3-[4-(4-Pyridinyl)phenyl]-2-propenal

The title compound was prepared by a procedure analogous to Reference Example 31 by substituting 4-(4-pyridinyl)-benzaldehyde (prepared as described in WO 9828264) for the 4-(2-pyridinyl)-benzaldehyde of Reference Example 31. MS 210 (M+H)⁺.

REFERENCE EXAMPLE 33

(E)-3-[4-(5-Pyrimidinyl)phenyl]-2-propenal

The title compound was prepared by a procedure analogous to Reference Example 31 by substituting 4-(5-pyrimidinyl)-benzaldehyde (prepared as described in Reference Example 25) for the 4-(2-pyridinyl)-benzaldehyde of Reference Example 31. MS 211 (M+H)⁺.

REFERENCE EXAMPLE 34

(E)-3-(2-Phenylpyridin-5-yl)-2-propenal

The title compound was prepared by a procedure analogous to Reference Example 31 by substituting 2-phenyl-5-pyridinecarboxaldehyde (prepared as described in J. Med Chem. 1998, 41, 2390) for 4-(2-pyridinyl)-benzaldehyde of Reference Example 31. MS 210 (M+H)⁺.

REFERENCE EXAMPLE 35

(E)-3-(4-Quinolinyl)-2-propenal

The title compound was prepared by a procedure analogous to Reference Example 31 by substituting 4-quinolinecarboxaldehyde for the 4-(2-pyridinyl)-benzaldehyde of Reference Example 31. MS 184 (M+H)⁺.

REFERENCE EXAMPLE 36

(E)-3-[3-(2-Pyridinyl)phenyl]-2-propenal

The title compound was prepared by a procedure analogous to Reference Example 31 by substituting 3-(2-pyridinyl)benzaldehyde (prepared as described in Reference Example 23) for the 4-(2-pyridinyl)-benzaldehyde of Reference Example 31. MS 210 (M+H)⁺.

REFERENCE EXAMPLE 37

(E)-3-[3-(2-Pyrimidinyl)phenyl]-2-propenal

The title compound was prepared by a procedure analogous to Reference Example 31 by substituting 3-(2-pyrimidinyl)benzaldehyde (prepared as described in Reference Example 23) for the 4-(2-pyridinyl)benzaldehyde of Reference Example 31. MS 211 (M+H)⁺.

REFERENCE EXAMPLE 38

(E)-3-(7-Quinolinyl)-2-propenal

The title compound was prepared by a procedure analogous to Reference Example 31 by substituting 7-quinolinecarboxaldehyde (prepared as described in J. Med. Chem. 1993, 36, 3308) for the 4-(2-pyridinyl)-benzaldehyde of Reference Example 31. MS 184 (M+H)⁺.

REFERENCE EXAMPLE 39

(E)-3-[4-(4-Pyrimidinyl)phenyl]-2-propenal

The title compound was prepared by a procedure analogous to Reference Example 31 by substituting 4-(4-pyrimidinyl)benzaldehyde (prepared as described in Reference Example 24) for the 4-(2-pyridinyl)-benzaldehyde of Reference Example 31. MS 211 (M+H)⁺.

REFERENCE EXAMPLE 40

(E)-3-[1-(2-Pyrimidinyl)-1H-imidazol-4-yl]-2-propenal

The title compound was prepared by a procedure analogous to Reference Example 31 by substituting 1-(2-pyrimidinyl)-1H-imidazole-4-carboxaldehyde (prepared as described in Reference Example 21) for 4-(2-pyridinyl)-benzaldehyde of Reference Example 31. MS 201 (M+H)⁺.

REFERENCE EXAMPLE 41

(E)-3-[5-(2-Pyridinyl)-pyridin-3-yl]-2-propenal
Step A: 3-Bromo-5-(2-pyridinyl)-pyridine A solution of 3,5-dibromopyridine (2.5 g, 10.5 mmol), PPh₃ (210 mg, 0.8 mmol) in degassed THF (2 mL) was treated with Pd₂(dba)₃ (Tris(dibenzylideneacetone) dipalladium (0), 91.5 mg, 0.1 mmol) at 25° C. under N₂. A solution of 2-pyridinyl zinc chloride (21 mL, 0.5 M in THF, Aldrich) in THF was added and the resulting solution was warmed to reflux for 16 h. The solution was allowed to cool to room temperature, diluted with EtOAc (200 mL), washed with water (2×100 mL), dried (MgSO₄), filtered and was concentrated in vacuo. Purification by flash chromatography (EtOAc) afforded the title compound as a white solid. MS 236 (M+H)⁺.
Step B: 1-(Tributylstannyl)-3,3-diethoxyprop-1-ene 1-(Tributylstannyl)-3,3-diethoxyprop-1-ene was prepared as described in J. Chem. Soc., Perkin Trans. 1,1990, 1, 187. CuCN (3.22 g, 36 mmol) in tetrahydrofuran at −78° C. was treated with n-butyllithium (28.8 mL, 72 mmol) via a syringe under N₂. After addition was complete the reaction mixture was allowed to warm until it became homogeneous and the resulting solution was recooled to −78° C. The reaction mixture was treated with tributyltin hydride (19.5 mL, 72 mmol) and was allowed to stir for 15 min. at −78° C. The pale yellow solution was treated with diethyl propyne acetal (5 g, 5.3 mmol) via a syringe and the reaction mixture was allowed to stir for 3 h at −78° C. The reaction was quenched by the addition of 9:1 satd. aqueous NH₄Cl:NH₄OH (15 mL) and was allowed to warm to 25° C. The resulting mixture was diluted with ethyl acetate (100 mL), washed with 9:1 satd. aqueous NH₄Cl NH₄OH (2×100 mL), dried (Na₂SO₄), filtered, and concentrated in vacuo. Purification by flash chromatography (0–5% EtOAc/ hexanes) afforded the title compound (5.2 g, 46%) as a pale yellow oil. MS 346 (M+H)+.

Step C: (E)-3-[5-(2-Pyridinyl)-pyridin-3-yl]-2-propenal

A mixture of Pd$_2$(dba)$_3$ (36 mg, 0.04 mmol) and PPh$_3$ (triphenylphosphine) in DMF (degassed, 2.0 mL) was allowed to stir for 5 min. at 25° C. 1,1'-Diethyl 3-(tributyltin)-propenylacetal (0.44 g, 1.27 mmol) and 3-bromo-5-(2-pyridinyl)-pyridine (100 mg, 0.42 mmol) were added and the resulting mixture was warmed to 80° C. After 18 h, the reaction mixture was allowed to cool to 25° C., diluted with ethyl acetate (100 mL), washed with brine (1×50 mL) and concentrated in vacuo. The residue was dissolved in 2N aqueous HCl (2.0 mL) and allowed to stir for 30 min. The reaction mixture was neutralized by the addition of sodium bicarbonate until the pH ~7, diluted with ethyl acetate (100 mL), washed with brine (1×50 mL), and concentrated in vacuo. Purification by flash chromatography (0–50% EtOAc/hexanes) afforded the title compound (10 mg) as a white solid. MS 211 (M+H)+.

REFERENCE EXAMPLE 42

3-(3-Pyridinyl)-2-propynal

Step A: 3-(3-Pyridinyl)-2-propynol

A solution of 3-bromopyridine (2.0 g, 12.6 mmol), propargyl alcohol (1.1 mL, 19 mmol), diisopropylethylamine (3.2 mL, 23 mmol), copper iodide (133 mg, 0.7 mmol) and tri-(t-butyl)phosphine (286 mg, 1.4 mmol) in degassed THF (10 mL) was treated with Pd(CH$_3$CN)$_2$Cl$_2$ (181 mg, 0.7 mmol) at 25° C. under N$_2$. After 18 h, the reaction mixture was filtered through celite, washed with ethyl acetate (2×100 mL), and concentrated in vacuo. Purification by flash chromatography (EtOAc) afforded the title compound (1.33 g, 80%) as a yellow oil. MS 134 (M+H)+.

Step B: 3-(3-Pyridinyl)-2-propynal

A solution of 3-(3-pyridinyl)-2-propynol (500 mg, 3.75 mmol) in CH$_2$Cl$_2$ (5 mL) was treated with activated manganous dioxide (3.3 g, 34.5 mmol) at 25° C. After 12 h, the reaction mixture was filtered through celite, washed with CH$_2$Cl$_2$ (2×50 mL), concentrated in vacuo. Purification by flash chromatography afforded the title compound (100 mg, 20%) as yellow brown oil. MS 133 (M+H)+.

REFERENCE EXAMPLE 43

3-Bromo-5-(2-pyrimidinyl)pyridine

Step A: 3-Bromo-5-cyanopyridine

5-Bromo-3-pyridinylcarboxamide (10 g, 49.7 mmol) in phosphorus oxychloride (25 mL) was warmed to reflux for 18 h, allowed to cool to 25° C., concentrated in vacuo and carefully treated with satd. aqueous sodium bicarbonate (~500 mL) until neutralized. The reaction mixture was diluted with CH$_2$Cl$_2$ (200 mL), stirred for 4 h, and the layers were separated. The aqueous layer was washed with CH$_2$Cl$_2$ (2×100 mL), and the organic layers were combined and dried (MgSO$_4$). The resulting solution was concentrated in vacuo to afford the title compound (6.35 g, 70%) as a white solid. MS 184 (M+H)+.

Step B: 3-Amidino-5-bromopyridine

Gaseous HCl was bubbled into absolute ethanol (500 mL) at 0° C. until saturated (~2 h). To the resulting solution was added the product of step A (5.0 g, 27.5 mmol), and the mixture allowed to warm to 25° C. After 48 h, the reaction mixture was concentrated in vacuo, washed with Et$_2$O (2×100 mL), and diluted with a methanolic solution of ammonia (100 mL, 7M in methanol, Aldrich). After 1 h, the reaction mixture was warmed to reflux for 12 h, allowed to cool to 25° C., and concentrated in vacuo to afford the title compound (4.82 g) as a white solid. The solid was used without any further purification. MS 201 (M+H)+

Step C: 3-Bromo-5-(2-pyrimidinyl)pyridine

A mixture of the product of Step B (4.86 g, 20.5 mmol) and 1,1,3,3-tetramethoxypropane (6.59 mL, 40 mmol) in DMF (25 mL) was warmed to 90° C. under N$_2$. After 18 h, the reaction mixture was allowed to cool to 25° C., concentrated in vacuo. Purification of the residue by flash chromatography (EtOAc) afforded the title compound (1.05 g, 22%) as a white solid. MS 237 (M+H)+

REFERENCE EXAMPLE 44

(E)-3-(4-isoquinolinyl)-2-propenal

The title compound was prepared by a procedure analogous to Reference Example 31 by substituting 4-isoquinolinecarboxaldehyde for 4-(2-pyridinyl)-benzaldehyde of Reference Example 31. MS 184 (M+H)+.

REFERENCE EXAMPLE 45

(E)-3-[(2-Fluoro-4-pyrimidin-2-yl)phenyl]-2-propenal

Step A:

Dimethyl sulfoxide (70 mL) and 4-bromo-2-fluorobenzaldehyde (2.44 g, 12.02 mmol) were added to a mixture of potassium acetate (3.54 g, 36.07 mmol), bis (pinacolato)diboron (3.36 g, 13.23 mmol), and [1,1'-bis (diphenylphosphino)ferrocene]dichloropalladium(II) (294 mg, 0.36 mmol). The mixture was heated to 80° C. for 18 h. The cooled reaction mixture was diluted with benzene, washed with water, dried (MgSO$_4$), and concentrated. The material was used in the next step without further purification.

Step B:

A mixture of the product of Step A (3.0 g, 12.02 mmol) and Na$_2$CO$_3$ (2.54 g, 24.04 mmol) in water (12 mL) were added to a solution of 5-bromopyrimidine (3.00 g, 18.87 mmol) and tetrakis(triphenylphosphine)palladium(0) (0.72 g, 0.62 mmol) in DME (30 mL) and the mixture was heated to reflux for 24 h. The cooled reaction mixture was diluted with dichloromethane, washed with sat. aq. NaHCO$_3$ and brine, dried (MgSO$_4$), and concentrated. Purification by chromatography (SiO$_2$, 1:1 hexane/ethyl acetate) yielded 1.52 g (63%) of 2-fluoro-4-(pyrimidin-2-yl)benzaldehyde. MS 203 (M+H)+.

Step C:

The title compound was prepared by a procedure analogous to Reference Example 30 by substituting 2-fluoro-4-(pyrimidin-2-yl)benzaldehyde for the 4-(2-pyridinyl)-benzaldehyde of Reference Example 30. MS 229 (M+H)+.

REFERENCE EXAMPLE 46

(E)-3-[1-(2-pyrazinyl)-imidazol-4-yl]-2-propenal

Step A: 1-(2-pyrazinyl)-1H-imidazole-4-carboxaldehyde

Sodium hydride (60% in oil, 720 mg, 18.0 mmol) was added to a 0° C. solution of 1H-imidazole-4-carboxaldehyde (2.20 g, 18.0 mmol) in DMF (8 mL). After stirring for 20 min at 0° C., the mixture was allowed to warm to RT and a solution of 2-chloropyrazine (2.06 g, 17.9 mmol) in DMF (4 mL) was added. The resulting mixture was heated to 100° C. for 18 h. The solvent was evaporated, the residue was dissolved in ethyl acetate, washed with water and brine, dried (MgSO$_4$), and concentrated to provide 3.10 g (86%) of the title compound. MS 175 (M+H)+

Step B: (E)-3-[1-(2-pyrazinyl)-imidazol-4-yl]-2-propenal

The title compound was prepared by a procedure analogous to Reference Example 31 by substituting 1-(2-pyrazinyl)-1H-imidazole-4-carboxaldehyde for 4-(2-pyridinyl)-benzaldehyde of Reference Example 31. MS 201 (M+H)+.

REFERENCE EXAMPLE 47

(E)-3-(4-(1,3,4-triazol-1-yl)phenyl-2-propenal

The title compound was prepared by a procedure analogous to Reference Example 31 by substituting 4-(1,3,4-triazol-1-yl)benzaldehyde (prepared as described in WO9526360) for 4-(2-pyridinyl)-benzaldehyde of Reference Example 31. MS 200 (M+H)+.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula 1:

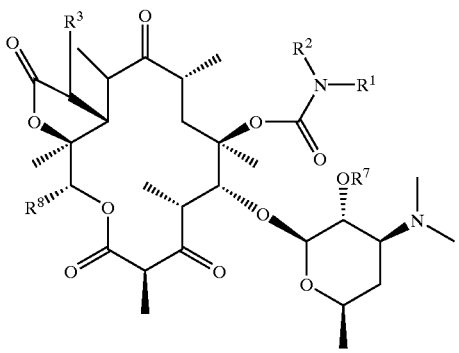

Formula 1 wherein $R^1$ and $R^2$ are independently selected from hydrogen, optionally substituted $C_1$–$C_8$-alkyl, optionally substituted —$CH_2$—$C_{2-8}$ alkenyl, and optionally substituted —$CH_2$—$C_{2-8}$ alkynyl, wherein the substituents are selected from the group consisting of $C_1$–$C_8$ alkyl, —$CH_2$—$C_{2-8}$ alkenyl, —$CH_2$—$C_{2-8}$ alkynyl, $C_3$–$C_8$ cycloalkyl, aryl, heteroaryl, substituted aryl, substituted heteroaryl, hydroxy, and $C_{1-8}$alkoxy;

$R^3$ is selected from hydrogen, $OR^4$, $SR^4$ and $NR^5R^6$, wherein $R^4$, $R^5$, and $R^6$ are independently selected from the group consisting of $C_{1-8}$alkyl, $C_{3-8}$alkenyl, and $C_{3-8}$ alkynyl, said $C_{1-8}$alkyl, $C_{3-8}$alkenyl, and $C_{3-8}$alkynyl being optionally substituted with one or more substituents selected from the group consisting of aryl, substituted aryl, heteroaryl, substituted heteroaryl, hydroxy, and $C_{1-6}$alkoxy;

$R^7$ is hydrogen or a hydroxy protecting group; and $R^8$ is selected from hydrogen, alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$)alkenyl, aryl($C_2$–$C_{10}$)alkynyl, heterocyclo($C_1$–$C_{10}$)alkyl, heterocyclo($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

or an optical isomer, enantiomer, diastereomer, racemate or racemic mixture thereof, or a pharmaceutically acceptable salt, esters or pro-drugs thereof.

2. The compound of claim 1 wherein $R^1$ and $R^2$ are independently selected from hydrogen, substituted $C_{1-8}$-alkyl, optionally substituted —$CH_2$—$C_{2-8}$alkenyl, and substituted —$C_2$—$C_{2-8}$alkynyl, wherein the substituents are selected from aryl, substituted aryl, heteroaryl, and substituted heteroaryl.

3. The compound of claim 2 wherein $R^3$ hydrogen or $OR^4$.

4. The compound of claim 2 wherein $R^7$ is hydrogen.

5. The compound of claim 2 wherein $R^8$ is ethyl.

6. The compound of claim 3, 4, or 5 wherein $R^1$ and $R^2$ are independently selected from hydrogen and substituted —$CH_2$—$C_{2-8}$alkenyl, wherein the substituents are substituted aryl or substituted heteroaryl.

7. The compound of claim 1 wherein $R^1$ and $R^2$ are independently selected from hydrogen, substituted $C_{1-8}$alkyl, optionally substituted —$CH_2$—$C_{2-8}$alkenyl, and substituted —$CH_2$—$C_{2-8}$alkynyl, wherein the substituents are selected from aryl, substituted aryl, heteroaryl, and substituted heteroaryl;

$R^3$ is hydrogen or $OR^4$; and $R^7$ is hydrogen.

8. The compound of claim 7 wherein $R^4$ is $C_{1-8}$alkyl.

9. The compound of claim 8 wherein $R^3$ is hydrogen.

10. The compound of claim 9 wherein $R^8$ is ethyl.

11. The compound of claim 10 wherein $R^1$ and $R^2$ are independently selected from hydrogen, (E)-3-[4-(2-pyrimidinyl)phenyl]-2-propenyl, (E)-3-[1-(2-pyrazinyl)-imidazol-4-yl]-2-propenyl, (E)-3-(4-isoquinolinyl)-2-propenyl, (E)-3-[1-(2-pyrimidinyl)-1H-imidazol-4-yl]-2-propenyl, and (E)-3-[3-(2-pyrimidinyl)phenyl]-2-propenyl.

12. The compound of claim 1 or a pharmaceutically acceptable salt thereof, which has the structure:

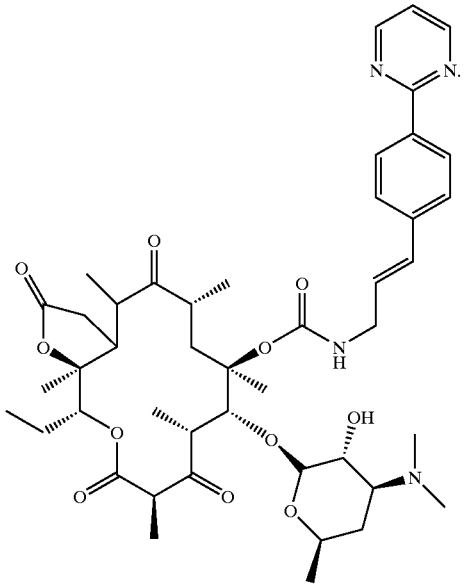

13. The compound of claim 1 or a pharmaceutically acceptable salt thereof, which has the structure:

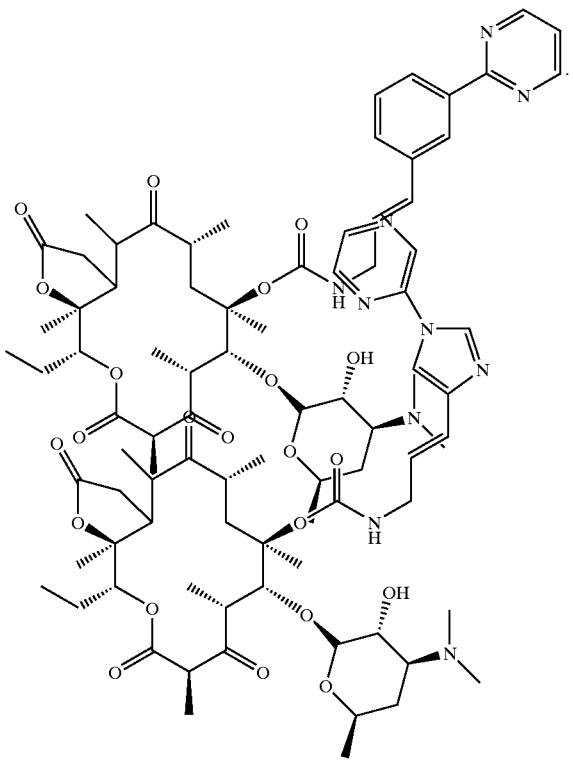

14. The compound of claim 1 or a pharmaceutically acceptable salt thereof, which has the structure:

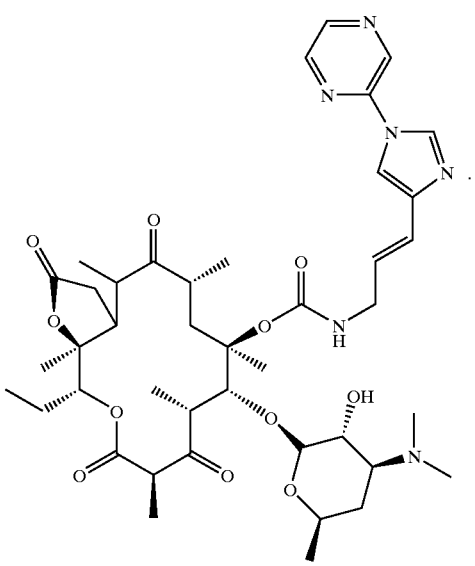

15. The compound of claim 1 or a pharmaceutically acceptable salt thereof, which has the structure:

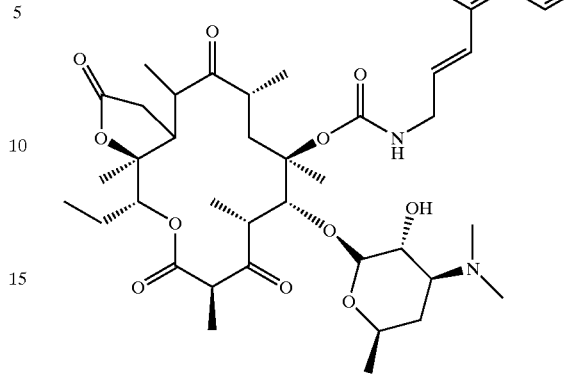

16. The compound of claim 1 or a pharmaceutically acceptable salt thereof, which has the structure:

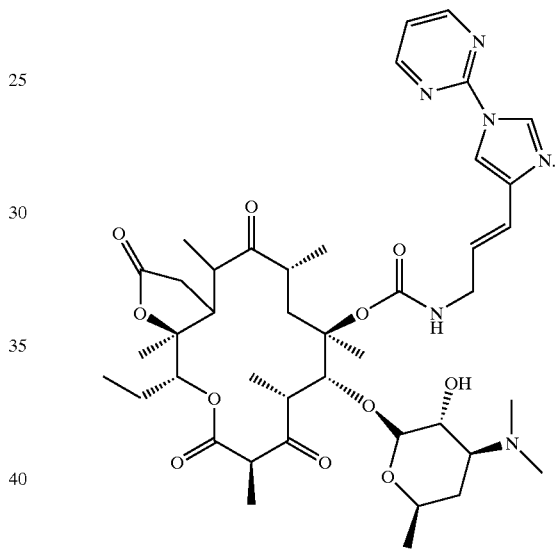

17. A pharmaceutical composition comprising a compound of claim 1 and a pharmaceutically acceptable carrier.

18. A method of treating a subject having a condition caused by or contributed to by bacterial infection, which comprises administering to said subject a therapeutically effective amount of the compound of Formula I as defined in claim 1.

19. The method of claim 18 wherein said condition is selected from community-acquired pneumonia, upper and lower respiratory tract infections, skin and soft tissue infections, meningitis, hospital-acquired lung infections, and bone and joint infections.

20. The method of claim 18 wherein said bacterium is selected from *S. aureus, S. epidermidis, S. pneumoniae, Enterococcus spp., Moraxella catarrhalis* and *H. influenzae.*

21. The method of claim 18 wherein said bacterium is a Gram-positive coccus.

22. The method of claim 21 wherein said Gram-positive coccus is antibiotic-resistant.

23. The method of claim 22 wherein said Gram-positive coccus is erythromycin-resistant.

24. A process for making a pharmaceutical composition comprising mixing any of the compounds according to claim 1 and a pharmaceutically acceptable carrier.

* * * * *